(12) United States Patent
Sakai

(10) Patent No.: US 7,684,057 B2
(45) Date of Patent: Mar. 23, 2010

(54) LINEAR MEASUREMENT APPARATUS

(75) Inventor: Yoshio Sakai, Shiki (JP)

(73) Assignee: Tanita Corporation, Tokyo (JP)

( * ) Notice: Subject to any disclaimer, the term of this patent is extended or adjusted under 35 U.S.C. 154(b) by 101 days.

(21) Appl. No.: 11/802,065

(22) Filed: May 18, 2007

(65) Prior Publication Data
US 2007/0291283 A1 Dec. 20, 2007

(30) Foreign Application Priority Data
Jun. 14, 2006 (JP) .............................. 2006-164416
Apr. 18, 2007 (JP) .............................. 2007-109893

(51) Int. Cl.
*G01B 11/14* (2006.01)
(52) U.S. Cl. ...................................... 356/614
(58) Field of Classification Search ......... 356/600–640; 367/99–116, 118–130
See application file for complete search history.

(56) References Cited

U.S. PATENT DOCUMENTS

| | | | | |
|---|---|---|---|---|
| 3,606,798 A | * | 9/1971 | Leiter | 74/112 |
| 3,724,958 A | * | 4/1973 | Callan | 356/639 |
| 3,802,774 A | * | 4/1974 | Eschler et al. | 356/637 |
| 4,047,029 A | * | 9/1977 | Allport | 378/90 |
| 5,210,593 A | * | 5/1993 | Kramer | 356/631 |
| 5,220,536 A | * | 6/1993 | Stringer et al. | 367/99 |
| 5,569,835 A | * | 10/1996 | Kenney et al. | 73/1.81 |
| 5,699,161 A | * | 12/1997 | Woodworth | 356/628 |
| 5,991,041 A | * | 11/1999 | Woodworth | 356/602 |
| 6,049,386 A | * | 4/2000 | Stringer et al. | 356/634 |
| 6,289,600 B1 | * | 9/2001 | Watts | 33/542 |
| 6,556,783 B1 | * | 4/2003 | Gelphman | 396/20 |
| 6,851,851 B2 | * | 2/2005 | Smith et al. | 378/189 |
| 6,920,197 B2 | * | 7/2005 | Kang et al. | 378/57 |
| 6,965,438 B2 | * | 11/2005 | Lee et al. | 356/625 |

(Continued)

FOREIGN PATENT DOCUMENTS

CN 1529806 A 9/2004

(Continued)

OTHER PUBLICATIONS

Nittetsu Hokkaido Control Systems Co., http://www.ncsfox.co.jp/product/dn/laser_c.html.

(Continued)

*Primary Examiner*—Gregory J Toatley, Jr.
*Assistant Examiner*—Jarreas C Underwood
(74) *Attorney, Agent, or Firm*—Hogan & Hartson LLP

(57) ABSTRACT

A linear measurement apparatus includes a measuring unit including at least one first noncontact distance measuring sensor and one second noncontact distance measuring sensor supported at a frame and aligned on opposite sides of a measured object. The measuring unit measures a plurality of first gap distances to a plurality of first object positions in a plurality of parallel first measurement lines and a plurality of second gap distances to a plurality of second object positions in a plurality of parallel second measurement lines. A distance calculator calculates a plurality of candidate object lengths on the basis of the first and second gap distances, each candidate object length being a distance between one of the first object positions and one of the second object positions. A maximum selector selects a maximum object length from among the plurality of candidate object lengths.

28 Claims, 16 Drawing Sheets

U.S. PATENT DOCUMENTS

| | | | |
|---|---|---|---|
| 7,104,453 B1 * | 9/2006 | Zhu et al. | 235/462.14 |
| 2001/0014137 A1 * | 8/2001 | Bjorkholm | 378/57 |
| 2004/0174537 A1 | 9/2004 | Ferger | |
| 2004/0184042 A1 * | 9/2004 | Kobayashi | 356/638 |

FOREIGN PATENT DOCUMENTS

| | | |
|---|---|---|
| JP | 9-273912 | 10/1997 |
| JP | 2004-294368 | 10/2004 |

OTHER PUBLICATIONS

Chinese Office Action dated Apr. 3, 2009.
Korean Office Action dated Jul. 28, 2009.

* cited by examiner

LINEAR MEASUREMENT APPARATUS

BACKGROUND OF THE INVENTION

1. Field of the Invention

The present invention relates to linear measurement apparatuses for measuring the dimensions of objects.

2. Description of Prior Art

Conventionally, contact measurement tools, such as tape measures and slide calipers, are used to easily measure the dimensions of objects. However, contact measurement tools may cause deformation of measured objects if the measured objects are deformable, so that measurement errors may be induced. The amount of deformation varies depending on the strength of force applied to the measured object, and it is difficult to compensate for such measurement errors.

Measurement apparatuses with noncontact distance measurement devices such as optical displacement sensors have been used industrially. For example, each of the Japanese Patent Applications JP-9-273912 (published in 1997) and JP 2004-294368 (published in 2004) discloses a thickness measurement apparatus that may be used in production lines of factories. The thickness measurement apparatus includes a pair of spaced optical displacement sensors located along a travel path of sheet materials. Sheet or plate materials are transferred through the gap between the sensors one by one, and each sensor measures the distance between the sensor itself and the material currently moving. On the basis of the measurements by the sensors, the thickness of the material is determined. A similar apparatus is disclosed in http://www.ncsfox.co.jp/product/dn/laser_c.html (Nittetsu Hokkaido Control Systems Co.). However, these conventional noncontact measurement apparatuses have been designed for measuring only objects of uniform thickness with simple contours.

SUMMARY OF THE INVENTION

Accordingly, the present invention provides a linear measurement apparatus that can measure, in a noncontact manner, a dimension of a nonuniform object having a complicated contour.

In accordance with one aspect of the invention, there is provided a linear measurement apparatus including: a frame which can be disposed around a measured object; a measuring unit including at least one pair of noncontact distance measuring sensors supported at the frame, the pair of noncontact distance measuring sensors including a first noncontact distance measuring sensor and a second noncontact distance measuring sensor, each sensor emitting light, receiving the light reflected from a measured object, and generating a signal corresponding to a distance from the corresponding sensor to the measured object, the first and second sensors being aligned on opposite sides of the measured object within the frame, the first sensor measuring a first gap distance between the first sensor and a first object position on the measured object in a first measurement line, the second sensor measuring a second gap distance between the second sensor and a second object position on the measured object in a second measurement line parallel to or identical to the first measurement line, the measuring unit measuring a plurality of first gap distances to a plurality of first object positions in a plurality of parallel first measurement lines and a plurality of second gap distances to a plurality of second object positions in a plurality of parallel second measurement lines lying on a plane identical to that in which the first measurement lines lie; a distance calculator for calculating a plurality of candidate object lengths on the basis of the plurality of first and second gap distances, each candidate object length being a distance between one of the first object positions and one of the second object positions; and a maximum selector for selecting a maximum object length from among the plurality of candidate object lengths. With such a structure, the linear measurement apparatus can measure dimensions of a nonuniform object to be measured having a complicated contour in a noncontact manner without deformation of the object to be measured.

In the specification and claims, the term "object length" or "length of the measured object" means any one of extent of the measured object whether it may be naturally called "width", "breadth", "depth", "thickness", or "height" of the measured object. In other words, the term "object length" or "length of the measured object" represents any one of the aforementioned terms.

The linear measurement apparatus may further include driving mechanisms for respectively moving the first and second noncontact distance measuring sensors with respect to the frame, in which the first sensor measures a plurality of first gap distances to a plurality of first object positions in a plurality of first parallel measurement lines, each first gap distance being between a sensor position of the first sensor and a first object position on the measured object, and in which the second sensor measures a plurality of second gap distances to a plurality of second object positions in a plurality of second parallel measurement lines, each second gap distance being between a sensor position of the second sensor and a second object position on the measured object. In this embodiment, each single sensor can measure a plurality of gap distances.

The linear measurement apparatus may further include a limit detector for determining whether or not at least one of the first and second noncontact distance measuring sensors has reached a limit of movement of the corresponding sensor; and a measurement terminator for terminating the corresponding sensor measuring the corresponding gap distance when the limit detector has detected that the corresponding sensor has reached the limit. In this embodiment, measurement of the gap distance can be terminated when the sensor has reached the limit of movement.

In another embodiment, the pair of noncontact distance measuring sensors may be fixedly supported at the frame in such a manner that the first measurement line in which the first gap distance is measured by the first sensor is identical to the second measurement line in which the second gap distance is measured by the second sensor. In this embodiment, the apparatus can be manufactured easily since the sensors are fixed to the frame. Although the sensors are fixed to the frame, they can be moved with respect to the measured object by moving the frame, so that each sensor can measure a plurality of gap distances.

In order to facilitate movement of the frame, the linear measurement apparatus may further include at least one guide for guiding movement of the frame with respect to the measured object.

The linear measurement apparatus may further include: an end detector for determining whether or not at least one of the first and second noncontact distance measuring sensors has reached an end of the measured object; and a measurement terminator for terminating the corresponding sensor measuring the corresponding gap distance when the end detector has detected that the corresponding sensor has reached the end of the measured object. In this embodiment, measurement of the gap distance can be terminated when the sensor has reached the end of the measured object.

Preferably, the end detector determines that the corresponding sensor has reached the end of the measured object when the corresponding sensor measures a first or second gap distance that is greater than a threshold value. In this embodiment, the end of the measured object can be detected easily.

The linear measurement apparatus may further include: a manual interface by which an operator may instruct to start and stop the first and second sensors; a measurement starter for starting the first and second sensors measuring the first and second gap distances when the operator has instructed to start the first and second sensors; and a measurement terminator for terminating the first and second sensors measuring the first and second gap distances when the operator has instructed to stop the first and second sensors. In this embodiment, measurement of the gap distance can be started and terminated manually in a simple manner.

In an embodiment, the measuring unit may include a plurality of pairs of the noncontact distance measuring sensors, each pair including the first and second noncontact distance measuring sensors fixedly supported at the frame, in which each of the first sensors measures a first gap distance between the corresponding first sensor and a first object position on the measured object in a first measurement line, and in which each of the second sensors measures a second gap distance between the corresponding second sensor and a second object position on the measured object in a second measurement line parallel to or identical to the first measurement line. In this embodiment, the apparatus can be manufactured easily since the sensors are fixed to the frame.

Preferably, the frame is of a shape in which one side is open, the frame having a pair of legs and a connection part connecting the legs, the first and second noncontact distance measuring sensors being supported on the legs, respectively. Since one side of the frame is open, the apparatus can be located around various measured objects easily. This feature is especially advantageous when, for example, the bed-ridden elderly or the physically handicapped are measured.

In an embodiment, the first measurement line in which the first gap distance is measured by the first sensor being parallel to and not identical to the second measurement line in which the second gap distance is measured by the second sensor, and in which the distance calculator calculates a parallel object length between the first and second object positions in a direction parallel to the first and second measurement lines on the basis of the first and second gap distances, and calculates one of the candidate object lengths on the basis of the parallel object length and a perpendicular object length between the first and second object positions in a direction perpendicular to the first and second measurement lines. In this embodiment, although the first measurement line is not arranged in the same straight line with the second measurement line, the distance calculator can calculate a candidate object length on the basis of the parallel and perpendicular object lengths. This embodiment can be used such that one of the first and second sensors is fixed, whereas the other is moved, and a plurality of candidate object lengths between a fixed object position and a variable object position are calculated. This embodiment can be also used in such a way that candidate object lengths between a first object position and a plurality of second object positions are calculated on the basis of a first gap distance and a plurality of second gap distances, and this calculation is repeated with reference to other first gap distances.

In another embodiment, the linear measurement apparatus may further include: an angle calculator for calculating an angle of a line between the first and second noncontact distance measuring sensors with respect to the frame on the basis of a distance between the first and second sensors in a first direction and a distance between the first and second sensors in a second direction perpendicular to the first direction; and sensor angle adjusters, each for adjusting an angle of a measurement line of one of the first and second sensors on the basis of the angle, so that the first measurement line in which the first gap distance is measured by the first sensor is identical to the second measurement line in which the second gap distance is measured by the second sensor. In this embodiment, the sensor angle adjusters adjust the angle of each of the first and second sensors for aligning the directions of the first and second gap distances, so that the distance calculator can precisely calculate a candidate object length between the first and second object positions in the same line between the first and second sensors.

The linear measurement apparatus may further include a frame-size adjustment mechanism for permitting the size of the frame to be adjusted. In this embodiment, measured objects of various sizes can be measured.

The linear measurement apparatus may further include a reference light emitter located at the frame for irradiating reference light onto the measured object in order to facilitate deployment of the linear measurement apparatus with respect to a reference position of the measured object. In this embodiment, deployment, i.e., positioning of the apparatus can be assisted by the reference light.

The linear measurement apparatus may further include a frame-inclination adjustment mechanism for permitting an inclination of the frame to be adjusted with respect to the measured object. In this embodiment, measurements can be made along various planes of inclination.

The linear measurement apparatus may further include: a display for displaying the maximum object length; and a display controller for controlling the display such that the display holds the displayed maximum object length for a period of time. In this embodiment, since the display holds the displayed maximum object length at least temporarily, an operator can easily confirm the displayed value after completion of measurement, and it is possible to avoid change of the displayed image even if the sensors are moved accidentally after completion of measurement.

The linear measurement apparatus may further include: a display; and a display controller for controlling the display such that a cross section of the measured object defined by the first object positions and the second object positions is displayed as a two-dimensional image on the basis of the first gap distances and the second gap distances measured at the measuring unit. In this embodiment, an operator can easily recognize the cross section, i.e., outline of the measured object at a glance even though the cross section is complicated.

The linear measurement apparatus may further include: an additional measuring unit including at least a third noncontact distance measuring sensor supported at the frame, the third sensor emitting light, receiving the light reflected from whatever in front of the third sensor, and generating a signal corresponding to a distance from the third sensor to whatever in front of the third sensor, so that the third sensor measures a third gap distance between the third sensor and a measured position in a third measurement line, the additional measuring unit measuring a plurality of third gap distances to a plurality of measured positions in a plurality of parallel third measurement lines lying on a plane identical to that in which the first and second measurement lines lie; a measured-object-end detector for detecting a first end and a second end of the measured object on the basis of the plurality of third gap distances; and a length calculator for calculating a length of the measured object between the first and second ends of the measured object, in which the maximum selector selects the maximum object length from among the length of the measured object and the plurality of candidate object lengths, instead of or in addition to selecting a maximum from among the plurality of candidate object lengths. In this embodiment, the length, i.e., interval between the first and second ends of the measured object is used as a candidate for the maximum object length in addition to the candidate object lengths, whereby the precision of measurement is improved.

In accordance with another aspect of the invention, there is provided a linear measurement apparatus including: a supporting member that can be disposed in proximity to a measured object; a measuring unit including at least one noncontact distance measuring sensor supported at the supporting member, the sensor emitting light, receiving the light reflected from whatever in front of the sensor, and generating a signal corresponding to a distance from the sensor to whatever in front of the sensor, so that the sensor measures a gap distance between the sensor and a measured position in a measurement line, the measuring unit measuring a plurality of gap distances to a plurality of measured positions in a plurality of parallel measurement lines; a measured-object-end detector for detecting a first end and a second end of the measured object on the basis of an amount of each of the plurality of gap distances; and a length calculator for calculating a length of the measured object between the first and second ends of the measured object. With such a structure, the linear measurement apparatus can measure a dimension of a nonuniform measured object having a complicated contour in a noncontact manner without deformation of the measured object.

The linear measurement apparatus may further include a driving mechanism for moving the noncontact distance measuring sensor with respect to the supporting member, in which the sensor measures a plurality of gap distances to a plurality of measured positions in a plurality of parallel measurement lines. In this embodiment, a single sensor can measure a plurality of gap distances.

The linear measurement apparatus may further include a measurement terminator for terminating the sensor measuring the gap distance when the measured-object-end detector has detected that the sensor has reached the second end of the measured object after the sensor passed the first end of the measured object. In this embodiment, measurement of the gap distance can be terminated when the sensor has reached the second end of the measured object.

Preferably, the measured-object-end detector determines that the sensor has reached the first end of the measured object when the sensor measures a gap distance that is less than a threshold or outputs an error signal, and in which the measured-object-end detector determines that the sensor has reached the second end of the measured object when the sensor measures a gap distance that is greater than a threshold or outputs an error signal. In this embodiment, the ends of the measured object can be detected easily.

The linear measurement apparatus may further include: a manual interface by which an operator may instruct to start and stop the sensor; a measurement starter for starting the sensor measuring the gap distance when the operator has instructed to start the sensor; and a measurement terminator for terminating the sensor measuring the gap distance when the operator has instructed to stop the sensor. In this embodiment, measurement of the gap distance can be started and terminated manually in a simple manner.

The linear measurement apparatus may further include a supporting-member-size adjustment mechanism for permitting the size of the supporting member to be adjusted. In this embodiment, objects of various sizes can be measured.

In another embodiment, the measuring unit may include a plurality of the noncontact distance measuring sensors fixedly supported at the supporting member for measuring a plurality of gap distances to a plurality of measured positions in a plurality of parallel measurement lines, respectively. In this embodiment, the apparatus can be manufactured easily since the sensors are fixed to the supporting member.

Preferably, the supporting member is of a shape in which one side is open, the supporting member having a pair of legs and a connection part connecting the legs, the noncontact distance measuring sensor being supported on the connection part. Since one side of the supporting member is open, the apparatus can be located around various measured objects easily. This feature is especially advantageous when the bedridden elderly or the physically handicapped are measured.

The linear measurement apparatus may further include a reference light emitter located at the supporting member for irradiating reference light onto the measured object in order to facilitate deployment of the linear measurement apparatus with respect to a reference position of the measured object. In this embodiment, deployment, i.e., positioning of the apparatus can be assisted by the reference light.

The linear measurement apparatus may further include a supporting-member-inclination adjustment mechanism for permitting an inclination of the supporting member to be adjusted with respect to the measured object. In this embodiment, measurements can be made along various planes of inclination.

The linear measurement apparatus may further include: a display for displaying the length of the measured object; and a display controller for controlling the display such that the display holds the displayed length of the measured object for a period of time. In this embodiment, since the display holds the displayed length of the measured object at least temporarily, an operator can easily confirm the displayed value after completion of measurement, and it is possible to avoid change of the displayed image even if the sensor is moved accidentally after completion of measurement.

The linear measurement apparatus may further include: a display; and a display controller for controlling the display such that the measured positions are displayed as a two-dimensional image on the basis of the gap distances measured at the measuring unit. In this embodiment, an operator can easily recognize the general outline of the measured object at a glance even though the cross section of the measured object is complicated.

BRIEF DESCRIPTION OF THE DRAWINGS

With reference to the accompanying drawings, various embodiments of the present invention will be described hereinafter. In the drawings.

DETAILED DESCRIPTION OF PREFERRED EMBODIMENTS

First Embodiment

Figure 1:
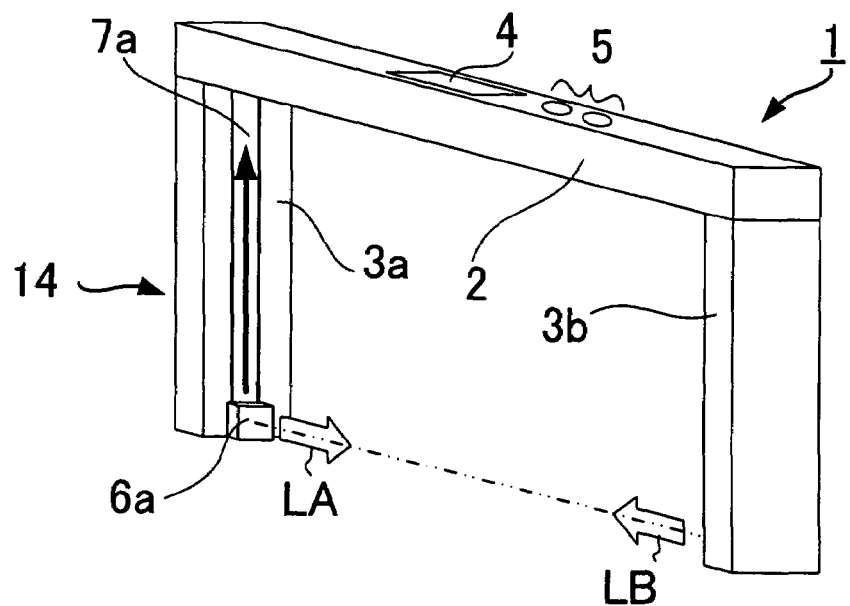
FIG. 1 is a perspective view of a linear measurement apparatus according to a first embodiment of the invention.
Figure 2:
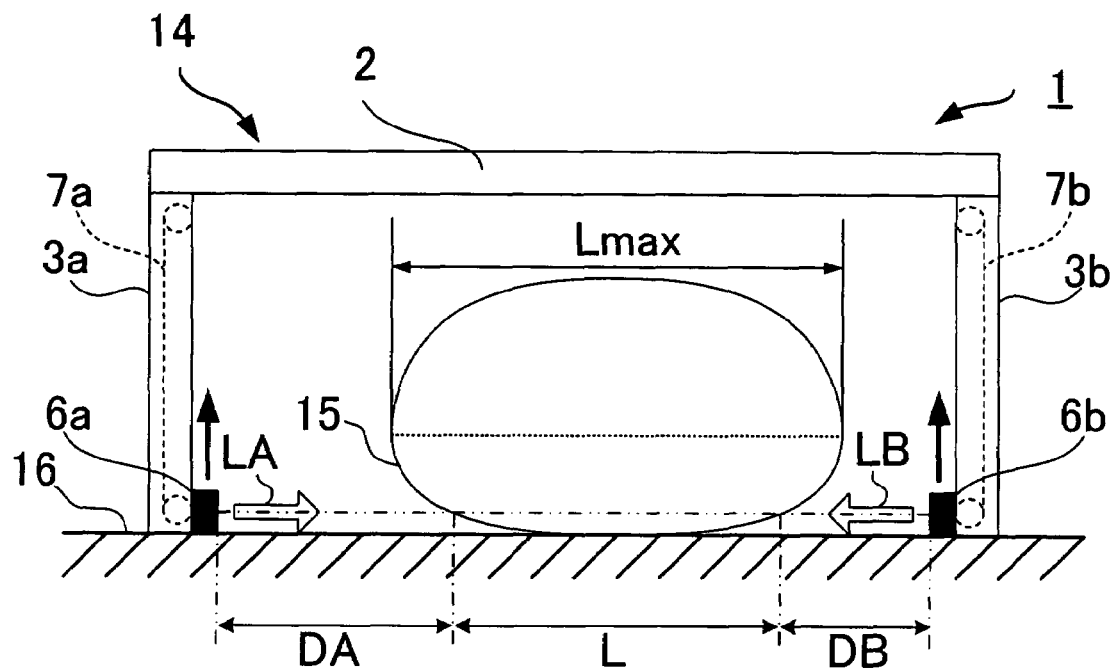
FIG. 2 is a front view of the linear measurement apparatus in FIG. 1 which has been set with respect to a measured object.
Figure 3:
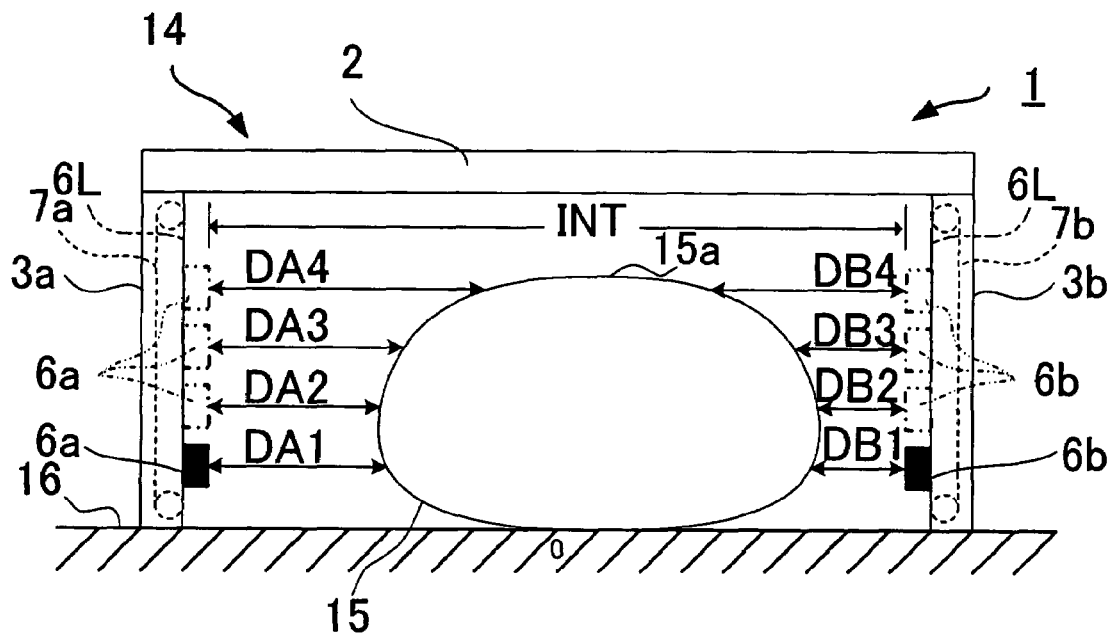
FIG. 3 is a front view of the linear measurement apparatus in FIG. 1 which is measuring distances.

As shown in FIGS. 1 through 3, a linear measurement apparatus 1 according to a first embodiment of the present invention includes a supporting member that is a portable frame 14 capable of being located around a measured object 15. The measured object 15 is a human subject who is lying on a floor or bed 16 in this embodiment, but any other suitable object can be measured.

The frame 14 is of a generally rectangular shape in which one side is open. More specifically, the frame 14 has a pair of parallel legs 3a and 3b vertically standing on the bed 16 and a connection part 2 of which both ends are connected to the legs 3a and 3b. By virtue of the open side of the frame 14, the apparatus 1 can be located around various measured objects easily. This feature is especially advantageous when the measured object 15 is a bed-ridden elderly person or physically handicapped person.

A console of the linear measurement apparatus 1 is provided at the connection part 2. The console includes a display 4 for displaying operation guidance, measurement results, or other information for the operator; and a manual interface 5 including at least one of buttons and switches by which the operator can provide commands to the apparatus for, e.g., turning on power or starting measurement. Inside the connection part 2, an electrical circuit, which will be described later, is provided for controlling the linear measurement apparatus 1.

The linear measurement apparatus 1 also includes a measuring unit for estimating the maximum object length Lmax shown in FIG. 2. The measuring unit includes a pair of noncontact distance measuring sensors, namely first and second sensors 6a and 6b supported on the legs 3a and 3b of the frame, respectively. The first and second sensors are aligned on opposite sides of the measured object 15 within the frame 14. Each sensor is an optical distance sensor that has a light emitter for emitting horizontally a light beam (such as for example, but not limited to, an infrared light beam) and a light receiver for receiving the light reflected from whatever in front of the sensor, such as the measured object 15, and for generating a signal corresponding to the distance from the corresponding sensor to whatever in front of the sensor. Thus, each sensor measures the gap distance between the corresponding sensor and whatever in front of the sensor.

In FIGS. 1 and 2, arrows LA and LB represent the light beams horizontally emitted from the sensors 6a and 6b. In the state shown in FIG. 2, the first sensor 6a measures a first gap distance DA between the first sensor 6a and a first object position on the measured object 15 with which a first horizontal measurement line (path of the light beam from the sensor 6a) intersects, and the second sensor 6b measures a second gap distance DB between the second sensor 6b and a second object position on the measured object 15 with which a second horizontal measurement line (path of the light beam from the sensor 6b) intersects. As shown in FIGS. 1 and 2, the first and second measurement lines are identical.

Driving mechanisms 7a and 7b are respectively located at the legs 3a and 3b for respectively moving the first and second noncontact distance measuring sensors 6a and 6b to an extent vertically with respect to the frame 14. For example, each driving mechanism includes an endless belt trained over pulleys driven by rotation means, e.g., a stepping motor and the corresponding sensor 6a or 6b is attached to the endless belt. Instead, other suitable driving mechanisms, known to those skilled in the art, may be used. By means of the driving mechanisms 7a and 7b, the first and second sensors 6a and 6b are raised and lowered synchronously along the legs 3a and 3b in the same vertical plane, as depicted by phantom lines in FIG. 3.

During the period in which the first sensor 6a is moved vertically, the first sensor 6a measures a plurality of first gap distances DA1 through DA4 to a plurality of first (left) object positions in a plurality of first parallel horizontal measurement lines on the same vertical plane, each first gap distance being between a sensor position of the first sensor 6a and a first (left) object position on the measured object 15. While the second sensor 6b is moved vertically, the second sensor 6b measures a plurality of second gap distances DB1 through DB4 to a plurality of second (right) object positions in a plurality of second parallel horizontal measurement lines on the same vertical plane identical to that in which the first measurement lines lie, each second gap distance being between a sensor position of the second sensor 6b and a second (right) object position on the measured object 15. Therefore, although the measuring unit has only two sensors, each single sensor can measure a plurality of gap distances to a plurality of object positions on the measured object 15 in a plurality of parallel horizontal lines. In FIG. 3, the first gap distances DA1 through DA4 and the second gap distances DB1 through DB4 are illustrated for exemplification, but it is to be understood that the number of gap distances is not limited to that in the illustrated embodiment.

Although the sensors 6a and 6b are moved, the horizontal distance-interval INT between them in a horizontal direction that is parallel to the first and second measurement lines remains unchanged since the supporting legs 3a and 3b are parallel. Thus, on the basis of the plurality of first and second gap distances DA and DB and the constant interval INT, it is possible to estimate a plurality of candidate object lengths L that are candidates for the maximum object length Lmax. For example, when the gap distances DA1 and DB1 are at the same elevation, a candidate object length is equal to INT minus DA1 minus DB1. Similarly, another candidate object length is equal to INT minus DA2 minus DB2. A third candidate object length is equal to INT minus DA3 minus DB3 whereas a fourth candidate object length is equal to INT minus DA4 minus DB4. As will be understood from FIG. 3, each candidate object length L is a distance between one of the first (left) object positions and one of the second (right) object positions.

The real maximum object length is nearly equal to the maximum among the above-mentioned plurality of candidate object lengths L. This is a generic principle of the maximum length measurement achieved by the apparatus 1. The precision of estimation of the maximum object length Lmax will be improved when the vertical distance-interval of the horizontal measurement lines is reduced and the number of measured gap distances is increased.

Figure 4:
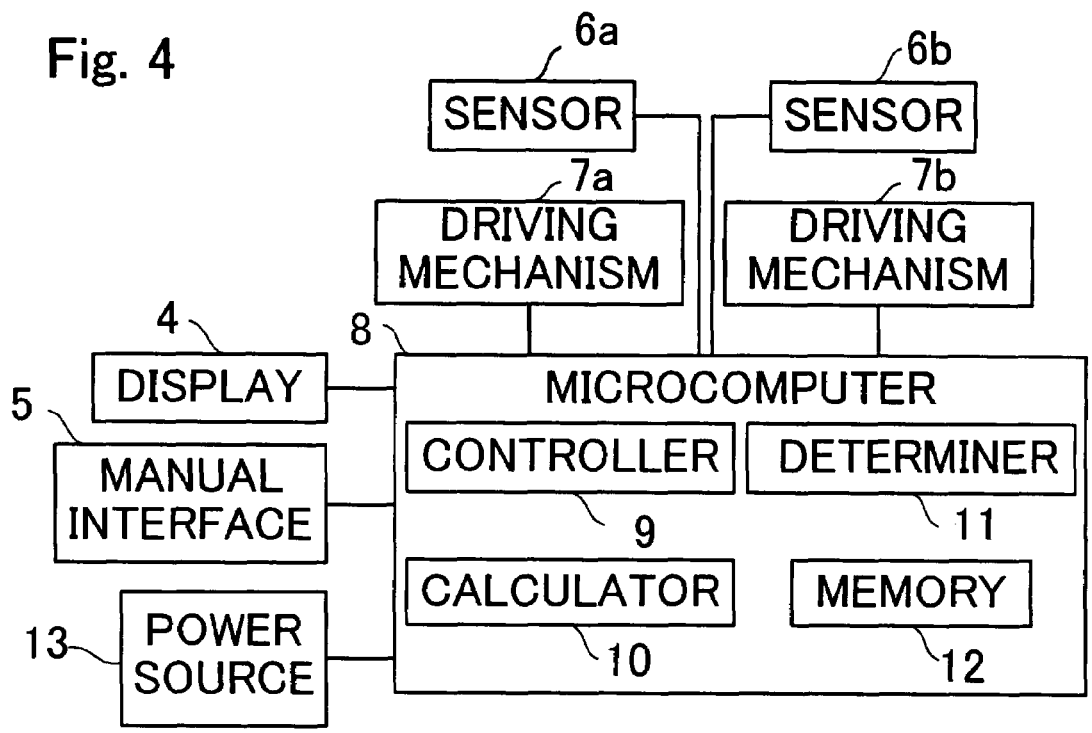
FIG. 4 is a block diagram showing elements of the linear measurement apparatus in FIG. 1.

With reference to the block diagram of FIG. 4, the electrical structure of linear measurement apparatus will be described. The above-mentioned electrical circuit within the connection part 2 includes a microcomputer 8 that is connected with the display 4, the manual interface 5, the sensors 6a and 6b, the driving mechanisms 7a and 7b. The microcomputer 8 is actuated by a power source 13 and includes a memory 12 and a processor that is functionally, but not physically, including a controller 9, a calculator 10, and a determiner 11.

The controller 9, i.e., the control means conducts overall control of the linear measurement apparatus 1. The overall control includes control of the sensors 6a and 6b for measuring the distances DA and DB and control of the driving mechanisms 7a and 7b for moving the sensors 6a and 6b.

The calculator 10 serves as a distance calculator, i.e., calculating means for calculating the plurality of candidate object lengths L on the basis of the plurality of first and second gap distances DA and DB measured by the sensors 6a and 6b.

The determiner 11 serves as a maximum selector, i.e., maximum selecting means for selecting the maximum object length Lmax from among the plurality of candidate object lengths L. The determiner 11 also serves as a limit detector, i.e., limit detecting means for determining whether or not at least one of the first and second sensors 6a and 6b has reached a limit of movement of the corresponding sensor. In this embodiment, the determiner 11 conducts such limit detection for each of the sensors 6a and 6b. If the determiner 11 has detected that a sensor has reached the limit of movement, the controller 9 serves as a measurement terminator, i.e., measurement terminating means for terminating the corresponding sensor measuring the corresponding gap distance.

The memory 12 stores in advance various data such as default values, system settings, and arithmetic expressions. Furthermore, the maximum value determined by the determiner 11 is stored in the memory 12.

The controller 9, the calculator 10, and the determiner 11 may be realized physically by a plurality of central processing units. Alternatively, they may be realized functionally by a computer program executed by a single central processing unit.

With reference to the flowchart shown in FIG. 5, use and operations of the linear measurement apparatus 1 will be described in more detail. The memory 12 permanently stores a computer program for controlling the linear measurement apparatus 1. The microcomputer 8 operates according to the computer program. Steps executed by the microcomputer 8 within the operations in the flowchart correspond to the computer program or an element of the computer program. In this embodiment, the memory 12 is used as a storage medium for storing the computer program or program element, but another memory or storage device may be used as such a storage medium. A semiconductor memory, hard disc, compact disc, digital versatile disc, flexible disc, or other suitable storage medium may be used for this purpose.

After manipulation of the power switch of the manual interface 5 for turning on power, the operator sets the linear measurement apparatus 1 on the bed 16 in such a manner that the frame 14 lies over the measured object 15 at step S1. The following operations are steps executed by the microcomputer 8 according to the program.

At step S2, the microcomputer 8 determines whether or not the measurement-start switch of the manual interface 5 has been pushed. If so, the process proceeds to step S3 where the microcomputer 8 initializes the entire system. For example, the microcomputer 8 initializes the positions of the sensors 6a and 6b and data in the memory 12.

After system initialization, at step S4, the microcomputer 8 serves as the controller 9 to control the driving mechanisms 7a and 7b for moving the sensors 6a and 6b synchronously, and serves to activate the sensors 6a and 6b for measuring or sampling one pair of the first gap distance DA and second gap distance DB.

As will be understood from the flowchart, whenever the process returns to step S4, the sensors 6a and 6b are moved synchronously and activated to measure the next pair of first gap distance and second gap distance, so that the measured object 15 is scanned at regular sampling time intervals. Each of the driving mechanisms 7a and 7b under control of the controller 9 moves the sensors 6a and 6b at the same speed, so that the sensors 6a and 6b are kept at the same elevation during such movement and measurement. The sampling period-interval multiplied by the movement speed of the sensors 6a and 6b is the sampling distance-interval (distance-interval of the horizontal measurement lines). For example, when the sampling distance-interval is one millimeter and the sampling period-interval is 50 milliseconds, the speed would be 0.02 meters per second.

At step S5, the microcomputer 8 serves as the calculator 10 for calculating the latest candidate object length L on the basis of the above-mentioned horizontal distance-interval INT and the pair of first and second gap distances DA and DB measured at the last time by the sensors 6a and 6b.

At step S6, the microcomputer 8 serves as the determiner 11 for determining whether or not the latest candidate object length L is the maximum object length Lmax in the measured cross section. In this embodiment, the value of the maximum object length is stored in the memory 12, and the determiner 11 determines whether or not the latest candidate object length is greater than the current maximum object length that has been stored in the memory 12. The default value of the value of the maximum object length in the memory 12 is zero.

If the latest candidate object length is greater, the process proceeds to step S7 where the determiner 11 erases the maximum object length stored previously in the memory 12 and stores in the memory 12 the latest candidate object length as the new maximum object length. That is, the determiner 11 renews the maximum object length in the memory 12. Then, the process proceeds to step S8. In contrast, if the latest candidate object length is not greater, the process proceeds to step S8 directly without renewing the maximum object length in the memory 12.

At step S8, the microcomputer 8 serves as the determiner 11 for determining whether or not the first and second sensors 6a and 6b have reached their limit 6L of movement (see FIG. 3). For example, a time period necessary for the sensors 6a and 6b to reach the limit 6L of movement is calculated on the basis of the traveling speed of the sensors 6a and 6b and the length from the start position and the limit 6L of movement. The necessary time period is stored in the memory 12, and the microcomputer 8 has a timer for counting elapsed time since the start of travel of the sensors 6a and 6b. When the elapsed time has reached the necessary time period, the determiner 11 determines that the sensors have reached the limit 6L.

If the sensors have not reached the limit 6L, the process returns to step S4 where the next first gap distance and the next second gap distance are measured. If the sensors have reached the limit 6L, the process proceeds to step S9 where the microcomputer 8 acts as a display controller for making the display 4 show the value of the maximum object length Lmax stored in the memory 12. The microcomputer 8 controls the display 4 such that the display holds the displayed maximum object length for a period of time. Since the display holds the displayed maximum object length at least temporarily, the operator can easily confirm the displayed value after completion of measurement, and it is possible to avoid change of the displayed image even if the sensors are moved accidentally after completion of measurement.

The maximum object length Lmax finally stored in the memory 12 and held in the display 4 is the maximum length of the measured object 15 located between the paths of the sensors 6a and 6b. After step S9, the process ends; the controller 9 serves as the measurement terminator and terminates the sensors 6a and 6b measuring the gap distances.

In the above-described first embodiment, the driving mechanisms 7a and 7b are driven synchronously to move the sensors 6a and 6b simultaneously, and the latest candidate object length is compared with the current maximum object length Lmax. However, the present invention is not intended to be limited to this embodiment. In an alternative embodiment, the controller 9 may drive the driving mechanisms 7a and 7b separately to move the sensors 6a and 6b at different times, but the sampling distance-interval and the sampling start elevation for the sensor 6a may be the same as those for the sensor 6b, so that the first parallel horizontal measurement lines of the sensor 6a coincide with the second parallel horizontal measurement lines of the sensor 6b. The microcomputer 8 may store all of the measured first gap distances DA and second gap distances DB consecutively in the memory 12. In this alternative embodiment, the calculator 10 may calculate all of the candidate object lengths L consecutively on the basis of the first and second gap distances DA and DB stored in the memory 12, in which each candidate object length is calculated on the basis of the above-mentioned horizontal distance-interval INT and first and second gap distances DA and DB on the same elevation, and the determiner 11 may select the maximum object length Lmax from among all of the calculated candidates.

In the above-described first embodiment, the sensors 6a and 6b are actuated automatically by the driving mechanisms 7a and 7b that are controlled by the controller 9. In an alternative embodiment (not shown), the sensors 6a and 6b may be moved manually by the operator while each sensor samples the corresponding gap distances at regular sampling distance-intervals. It is preferable to provide a means or mechanism for restricting the speed of the sensors 6a and 6b in order to facilitate such equally spaced measurement. For example, at least one speed meter (not shown) may be used which measures the speed of at least one of sensors 6a and 6b and supplies a signal indicative of the speed to the microcomputer 8. When the speed exceeds a threshold, the microcomputer 8 may send a notice to the operator, e.g., may cause the display 4 to display an error message to avoid unreliable measurement.

In another alternative embodiment, the determiner 11 may serve as an end detector, i.e., an end detecting means that determines whether or not at least one of the first and second noncontact distance measuring sensors 6a and 6b has reached an end 15a of the measured object 15. Preferably, the end detector determines that the corresponding sensor 6a or 6b has reached the end 15a of the measured object 15 (shown in FIG. 3) when the corresponding sensor 6a or 6b measures a first or second gap distance DA or DB that is greater than a threshold value. More preferably, the end detector determines that both the sensors 6a and 6b have reached the end 15a of the measured object 15 when both the sensors 6a and 6b measure a first and second gap distances DA and DB that are greater than a half of the above-mentioned horizontal distance-interval INT between the fixed sensors 6a and 6b. In this case, the end 15a of the measured object 15 can be detected easily. The controller 9 may serve as a measurement terminator, i.e., measurement terminating means for terminating at least one of the sensors 6a and 6b measuring the corresponding gap distance DA or DB when the end detector has detected that the corresponding sensor DA or DB has reached the end 15a of the measured object 15. In this embodiment, measurement of the gap distance DA or DB can be terminated when the sensor 6a or 6b has reached the end 15a of the measured object 15.

Figure 6:
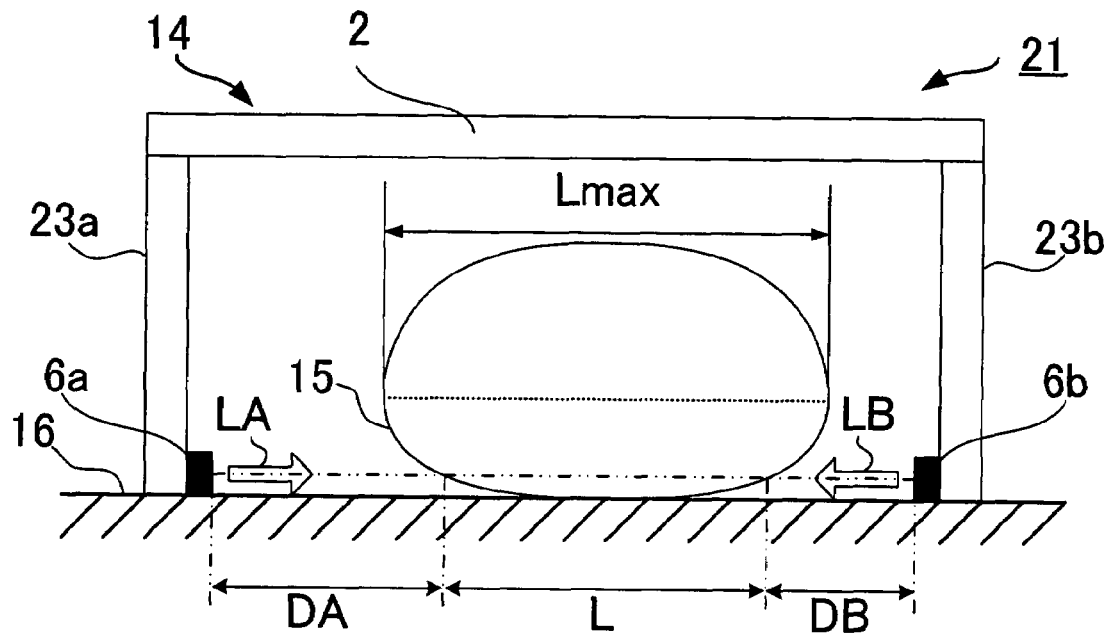
FIG. 6 is a front view of a linear measurement apparatus according to an alternative embodiment which has been set with respect to a measured object.
Figure 7:
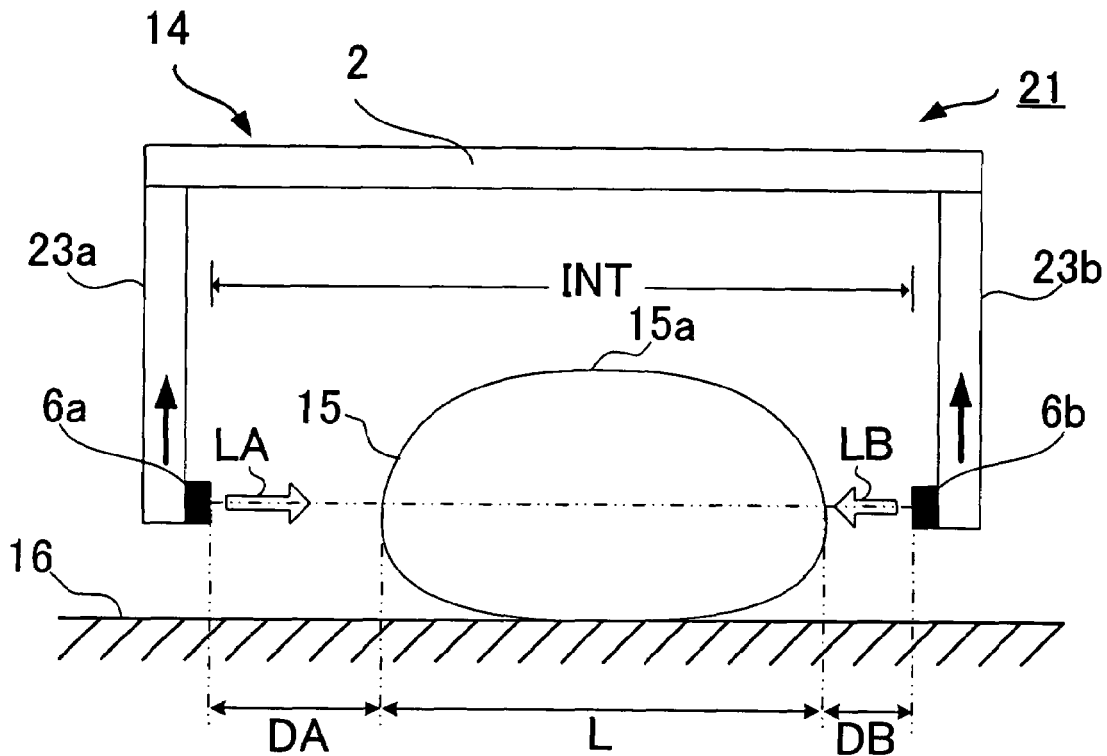
FIG. 7 is a front view of the linear measurement apparatus in FIG. 6 which is being raised and is measuring distances.

In another alternative embodiment of a linear measurement apparatus 21 shown in FIGS. 6 and 7, a pair of noncontact distance measuring sensors 6a and 6b are fixedly secured at legs 23a and 23b of the frame 14 in such a manner that the first measurement line in which the first gap distance DA is measured by the first sensor 6a is identical to the second measurement line in which the second gap distance DB is measured by the second sensor 6b. In this embodiment, the apparatus 21 can be manufactured easily since the sensors 6a and 6b are fixed to the frame 14. Although the sensors 6a and 6b are fixed to the frame 14, they can be moved along with the frame 14 in a group with respect to the measured object 15 as shown in FIG. 7, so that each sensor can measure the plurality of gap distances DA and DB. The operator may grip a part of the frame 14 and raise the linear measurement apparatus 21 substantially vertically and gradually from the bed 16. During lifting of the linear measurement apparatus 21, the sensors 6a and 6b sample the gap distances DA and DB.

In the embodiment of the linear measurement apparatus 21 shown in FIGS. 6 and 7, the determiner 11 preferably serves as the above-described end detector that determines whether or not at least one of the first and second noncontact distance measuring sensors 6a and 6b has reached an end 15a of the measured object 15. The controller 9 serves as the above-described measurement terminator for terminating at least one of the sensors 6a and 6b measuring the corresponding gap distance DA or DB when the end detector has detected that the corresponding sensor DA or DB has reached the end 15a of the measured object 15. In this embodiment, measurement of the gap distance DA or DB can be terminated when the sensor 6a or 6b has reached the end 15a of the measured object 15.

Figure 5:
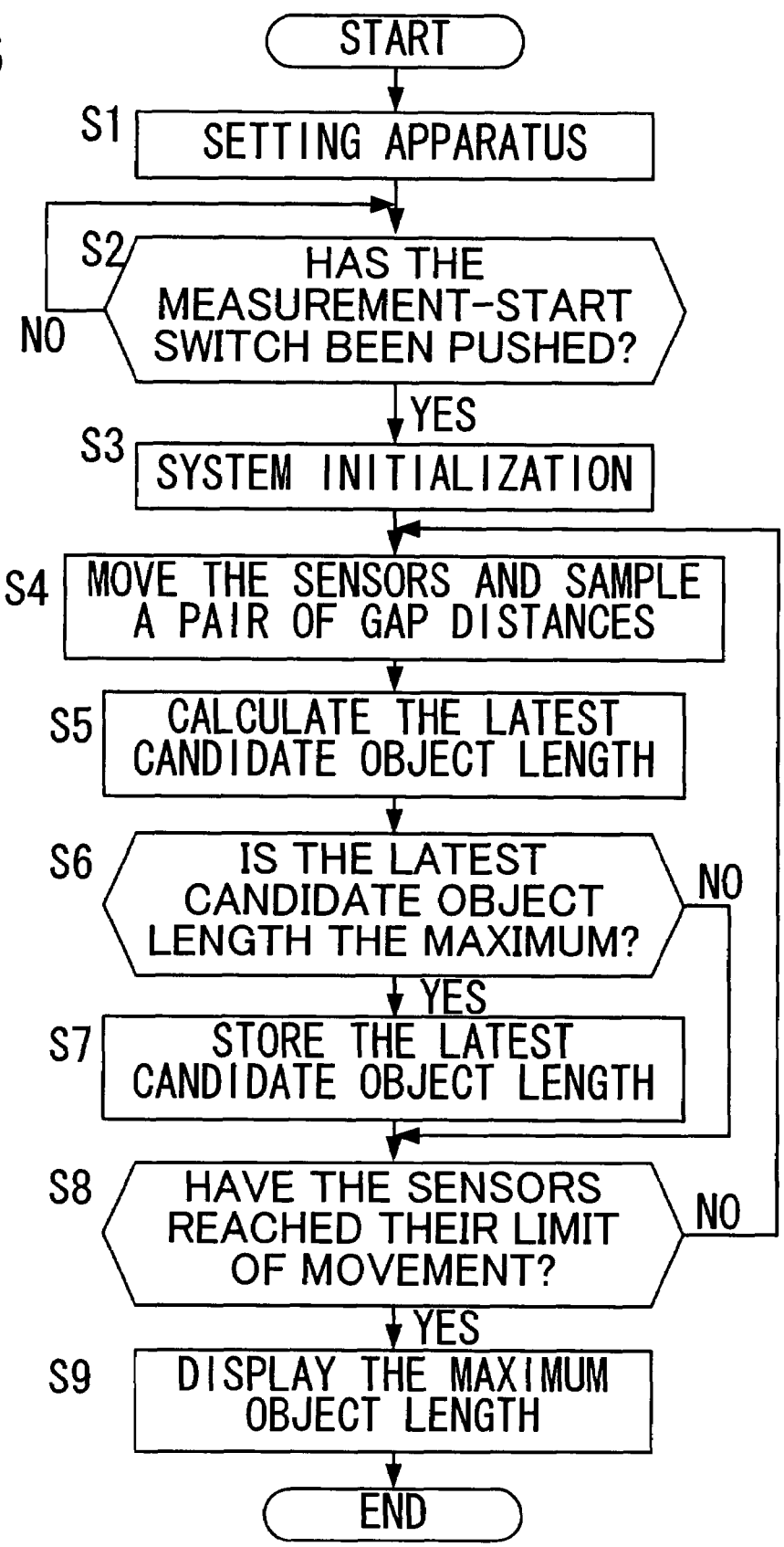
FIG. 5 is a flowchart showing use and operations of the linear measurement apparatus in FIG. 1.

The use and operations of the alternative embodiment shown in FIGS. 6 and 7 is similar to those of the first embodiment described above with reference to the flowchart illustrated in FIG. 5. However, at step S4, the automatic movement of the sensors 6a and 6b by the driving mechanisms 7a and 7b is replaced by the manual movement of the frame 14 together with the sensors 6a and 6b. In addition, the determination at step S8 for detecting the limit of movement is replaced by the determination by the end detector which determines that both the sensors 6a and 6b have reached the end 15a of the measured object 15.

Figure 8:
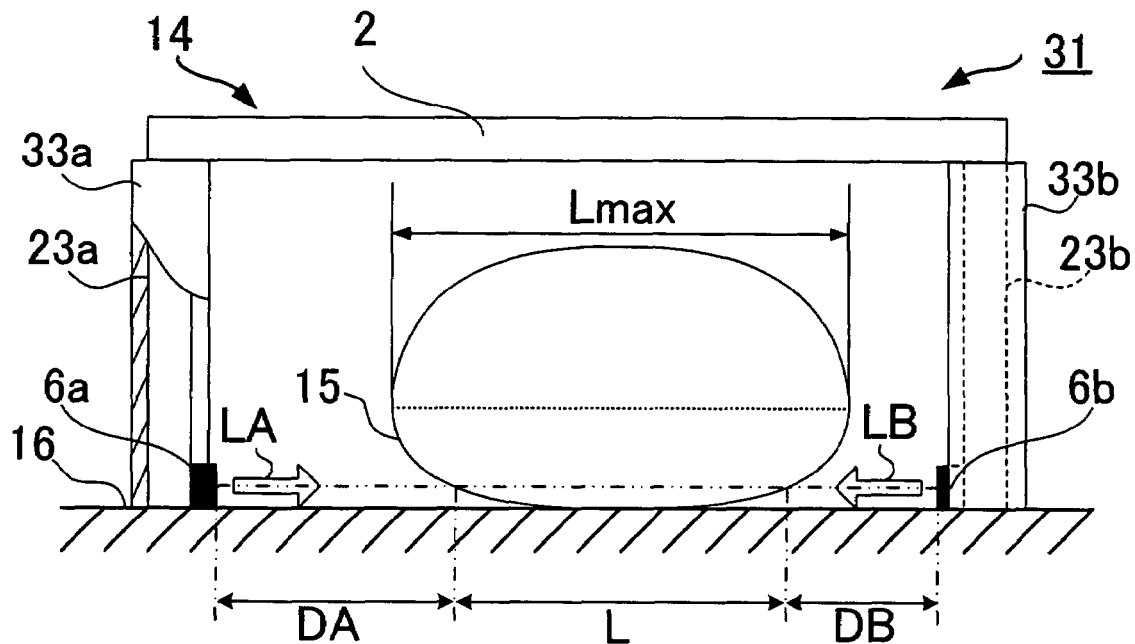
FIG. 8 is a front view of a linear measurement apparatus according to a modified embodiment which has been set with respect to a measured object.
Figure 9:
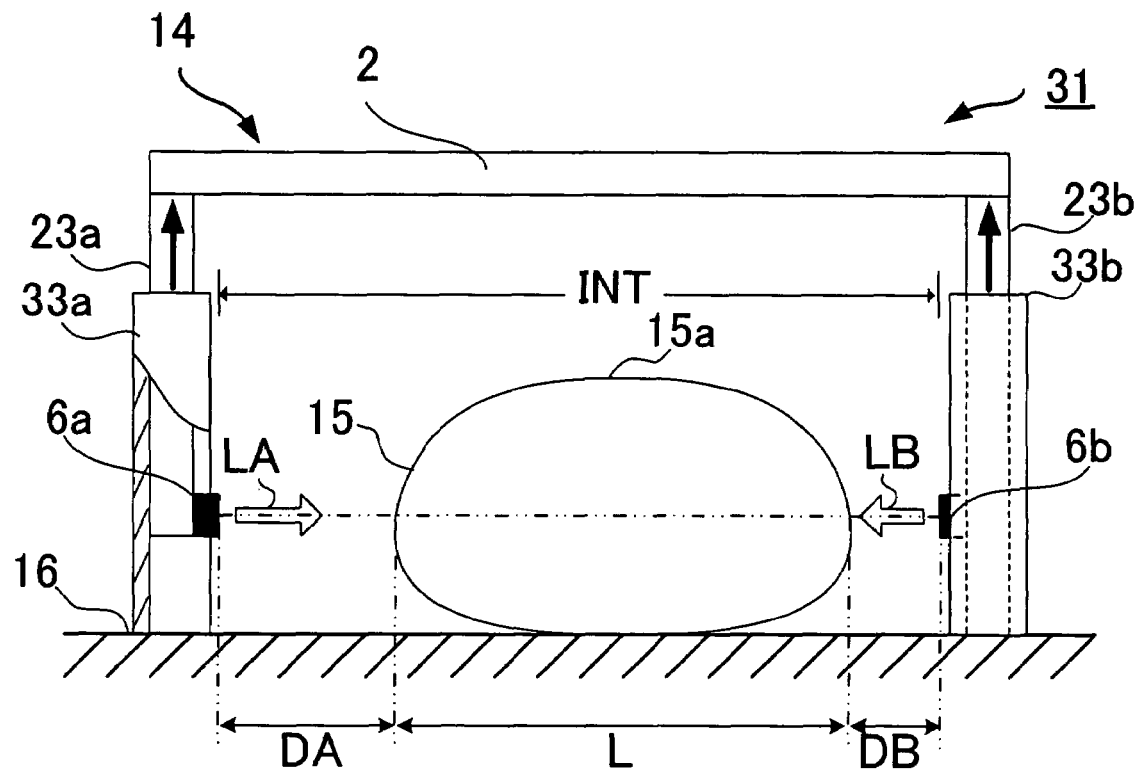
FIG. 9 is a front view of the linear measurement apparatus in FIG. 8 which is measuring distances.

FIGS. 8 and 9 show a modification of the embodiment shown in FIGS. 6 and 7. In this modified embodiment, a linear measurement apparatus 31 includes a pair of leg guides 33a and 33b for guiding vertical movement of the frame 14 with respect to the measured object 15 in order to facilitate lifting of the frame 14. The legs 23a and 23b are slidably inserted into the leg guides 33a and 33b, respectively. The leg guides 33a and 33b are formed in such a manner that the first and second measurement lines are not obstructed by the guides, so that the sensors 6a and 6b can measure the gap distances to the measured object 15.

In the above-described alternative embodiments shown in FIGS. 6 and 7 and FIGS. 8 and 9, it is also preferable to provide the above-mentioned means for restricting the speed of the sensors 6a and 6b in order to facilitate equally spaced measurement. In the above-described alternative embodiments shown in FIGS. 6 and 7 and FIGS. 8 and 9, it is also preferable to provide at least one handle or grip that will be grasped or held by the operator. The handle may be convenient for raising the apparatus stably.

Second Embodiment

Figure 10:
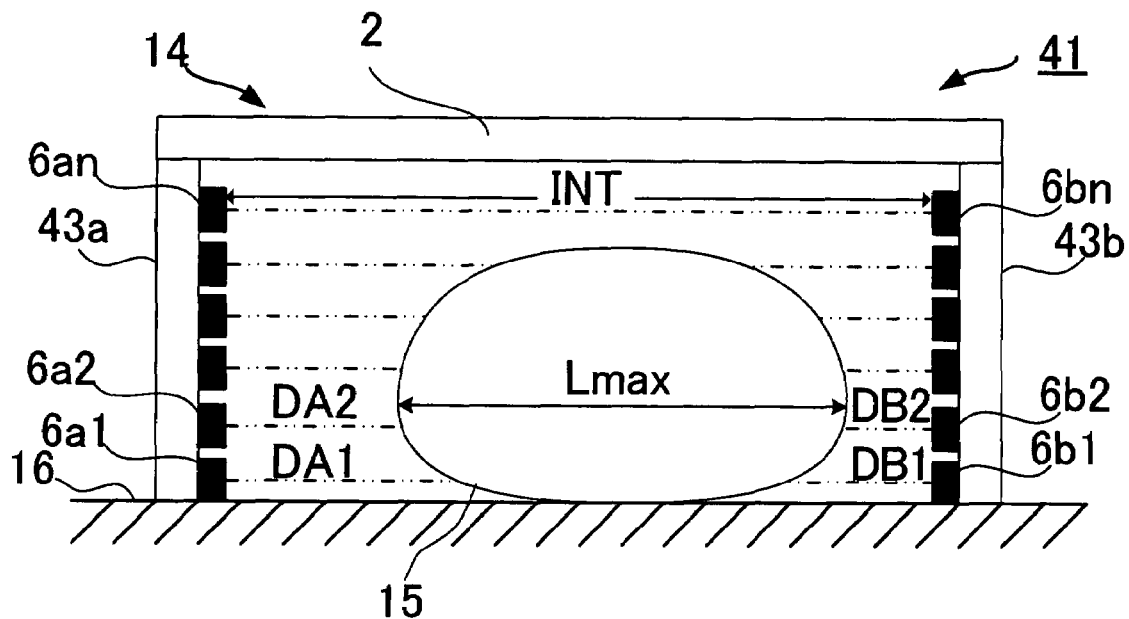
FIG. 10 is a front view of a linear measurement apparatus according to a second embodiment which has been set with respect to a measured object.

As shown in FIG. 10, a linear measurement apparatus 41 according to a second embodiment of the present invention includes a supporting member, i.e., portable frame 14 that is substantially the same as in the first embodiment. The linear measurement apparatus 41 also includes a measuring unit for estimating the maximum object length Lmax shown in FIG. 10. The measuring unit of this embodiment includes a plurality of pairs (n pairs) of noncontact distance measuring sensors, each pair including the first and second noncontact distance measuring sensors 6a and 6b fixedly secured to the legs 43a and 43b of the frame 14. The type of sensors employed is the same as that in the first embodiment.

The pairs are spaced equally with respect to each other. Each of the first sensors $6a1$ through $6an$ measures a first gap distance between the corresponding first sensor and a first object position on the measured object 15 with which a first horizontal measurement line (path of the light beam from the sensor 6a) intersects, and each of the second sensors $6b1$ through $6bn$ measures a second gap distance between the corresponding second sensor and a second object position on the measured object 15 with which a second horizontal measurement line (path of the light beam from the sensor 6b) intersects. The second measurement lines are parallel to or identical to the first measurement lines.

In this embodiment, the apparatus 41 can be manufactured easily since the sensors $6a1$ through $6an$ and $6b1$ through $6bn$ are fixed to the frame 14 and the above-described driving mechanisms 7a and 7b are excluded. In addition, the use of the apparatus is simplified since the automatic or manual movement of the sensors 6a and 6b (with or without the frame) is unnecessary. The precision of estimation of the maximum object length Lmax will be improved when the number of the pairs of the sensors is increased.

Figure 11:
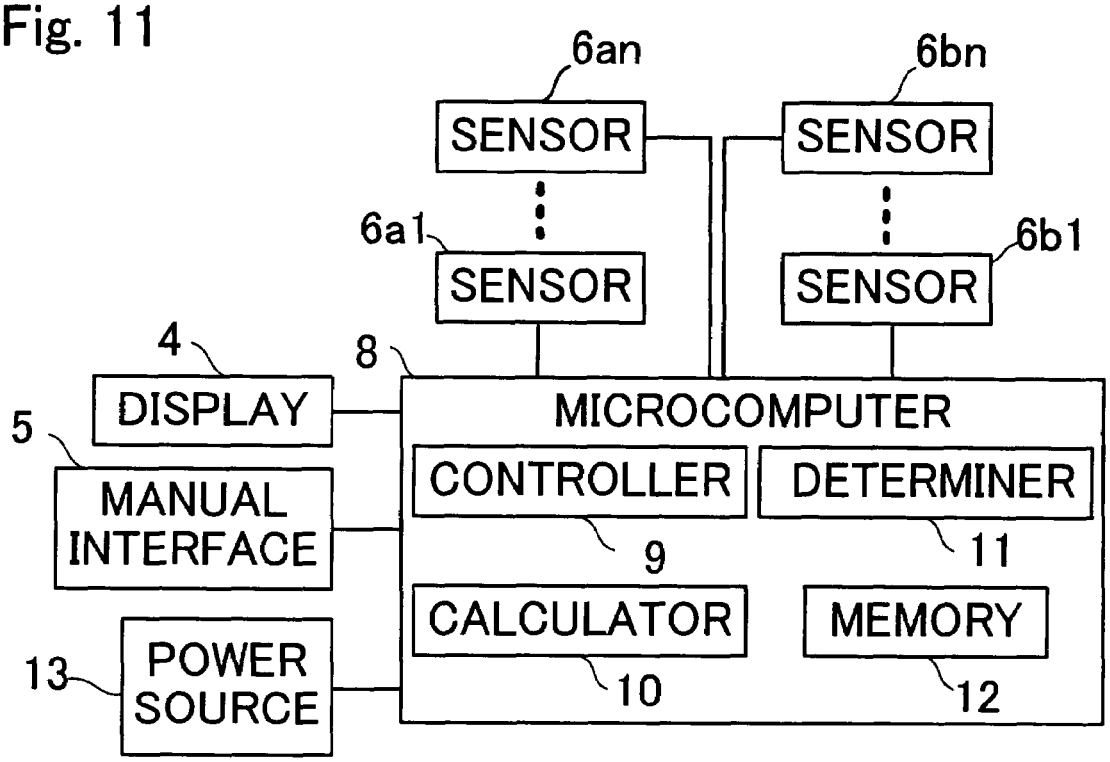
FIG. 11 is a block diagram showing elements of the linear measurement apparatus in FIG. 10.

With reference to the block diagram of FIG. 11, the electrical structure of the linear measurement apparatus will be described. The block diagram of FIG. 11 is similar to FIG. 5 of the first embodiment, but in FIG. 11 the driving mechanisms 7a and 7b are excluded and a greater number of the sensors $6a1$ through $6an$ and $6b1$ through $6bn$ are connected with the microcomputer 8.

Instead of controlling the driving mechanisms 7a and 7b, the controller 9 activates and deactivates the sensors sequentially in turns. Instead of detection of the movement limit, the determiner 11 serves as a completion detector, i.e., as a completion detecting means for determining whether or not all of the first and second sensors $6a1$ through $6an$ and $6b1$ through $6bn$ have finished sampling the gap distances.

Figure 12:
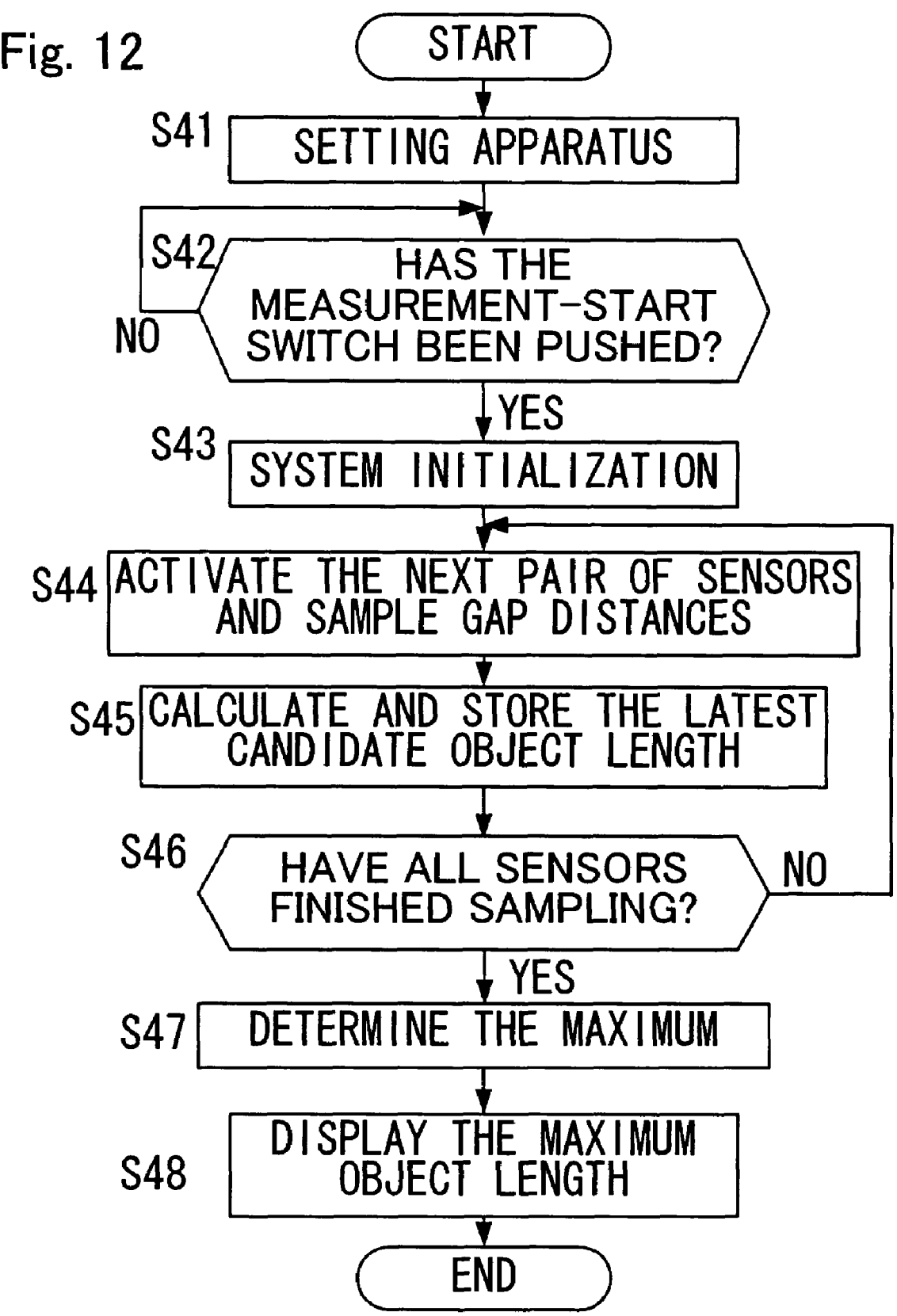
FIG. 12 is a flowchart showing use and operations of the linear measurement apparatus in FIG. 10.

With reference to the flowchart shown in FIG. 12, use and operations of the linear measurement apparatus 41 will be described in more detail. Steps executed by the microcomputer 8 within the operations in the flowchart correspond to the computer program or an element of the computer program stored in the memory 12 or another memory or storage device.

Steps S41, S42, and S43 after turning on power are the same as steps S1, S2, and S3 in FIG. 5 of the first embodiment, so that they are not described in detail. However, at step S43, it is unnecessary to initialize the positions of the sensors 6a and 6b. In addition, a counter is functionally or physically provided in the microcomputer 8 for counting the ordinal number "n" indicating a pair of first and second sensors which should be employed next. The counter number "n" is reset at zero (default value) at step S43 for system initialization.

At step S44, the microcomputer 8 increments the counter number "n" by one. Therefore, directly after system initialization, the counter number "n" becomes one. Then, the microcomputer 8 serves as the controller 9 to activate one pair of the first sensor 6a and the second sensor 6b that correspond to the counter number "n", and therefore, the first sensor 6a and the second sensor 6b measure or sample the corresponding first gap distance DA and the corresponding second gap distance DB, respectively. Other pairs of sensors are deactivated. Namely, the microcomputer 8 selects the next pair of sensors and activates the next pair of sensors. Directly after system initialization, activated are the first sensor 6a1 and the second sensor 6b1 that correspond to the counter number "one", and therefore, the first sensor 6a1 and the second sensor 6b1 measure or sample the corresponding first gap distance DA1 and the corresponding second gap distance DB1.

At step S45, the microcomputer 8 serves as the calculator 10 for calculating the latest candidate object length L on the basis of the above-mentioned horizontal distance-interval INT and the pair of first and second gap distances DA and DB measured at the last time by the sensors 6a and 6b. The calculator 10 stores in the memory 12 the latest candidate object length L as the n-th calculation result.

At step S46, the microcomputer 8 acts as the determiner 11 (completion detector) for determining whether or not all pairs of the first and second sensors 6a1 through 6an and 6b1 through 6bn have finished sampling the gap distances. This determination is achieved by comparing the counter number "n" with the maximum (the real number of the pairs).

If the determination at step S46 is negative, the process returns to step S44 where the next first gap distance and the next second gap distance are measured. If all the sensors have finished measuring, the process proceeds to step S47 where the microcomputer 8 acts as the determiner 11 for determining the maximum object length Lmax among the candidate object lengths stored in the memory 12 by comparing all the candidate object lengths.

Then, at step S48, the microcomputer 8 acts as a display controller for making the display 4 show the value of the maximum object length Lmax obtained. The microcomputer 8 controls the display 4 such that the display holds the displayed maximum object length for a period of time. Since the display holds the displayed maximum object length at least temporarily, the operator can easily confirm the displayed value after completion of measurement, and it is possible to avoid change of the displayed image even if the sensors are moved accidentally after completion of measurement.

The maximum object length Lmax held in the display 4 is the maximum length of the measured object 15 located between the column of first sensors 6a and the column of second sensors 6b. After step S48, the process ends.

In the above-described second embodiment, the microcomputer 8 stores all of the measured first gap distances DA and second gap distances DB consecutively in the memory 12, and the determiner 11 selects the maximum object length Lmax from among all of the calculated candidates. However, it is not intended to limit the present invention to this embodiment. In an alternative embodiment, the determiner 11 may compare the latest candidate object length with the current maximum object length Lmax, and may renew the maximum object length if the latest candidate object length is greater.

Figure 13:
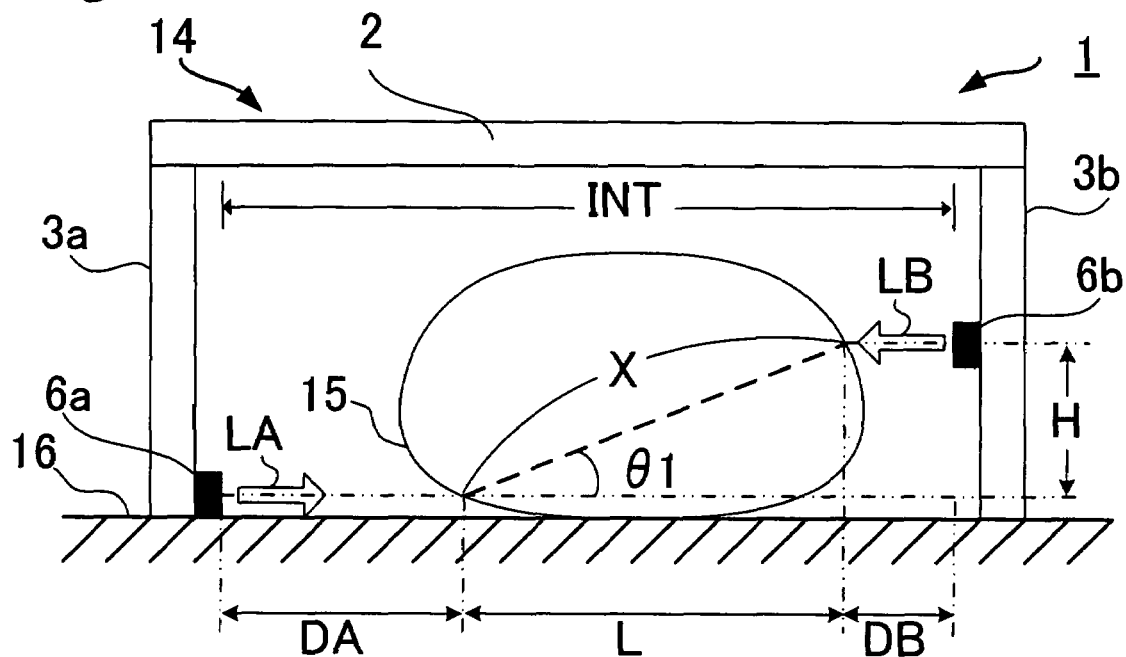
FIG. 13 is a front view of a linear measurement apparatus according to another modified embodiment which has been set with respect to a measured object.

FIG. 13 shows a modified embodiment. It should be noted that the modification in this modified embodiment is applicable to all of the first and second embodiments and the above-described alternative embodiments although the same reference symbols as in the first embodiment are used in FIG. 13. In all of the above-described embodiments, a candidate object length L is the length of the measured object 15 in the horizontal line which is the same as a first measurement line in which a first gap distance DA is measured by the first sensor 6a for calculating the candidate object length L and a second measurement line in which a second gap distance DB is measured by the second sensor 6b for calculating the candidate object length L.

In the modified embodiment, however, an oblique candidate object length X is determined on the basis a first gap distance DA and a second gap distance DB of which the first and second measurement lines are parallel to and not identical to each other. As shown in FIG. 13, let us assume that a second sensor 6B is located at an upper position, whereas a first sensor 6b is located at a lower position. The illustrated sensors 6a and 6b are employed for sampling first and second gap distances DA and DB in order to determine an oblique candidate object length X.

In this modified embodiment, the calculator 10 (distance calculator) calculates a parallel object length L between first and second object positions in a direction parallel to the first and second measurement lines on the basis of the first and second gap distances DA and DB since L equals INT minus DA minus DB. The elevational difference between the sensors 6a and 6b is a perpendicular object length H between the first and second object positions in a direction perpendicular to the first and second measurement lines. If the elevational difference is fixed, the perpendicular object length H is already known and may be stored in the memory 12. On the other hand, if the elevational difference is variable, the calculator 10 (distance calculator) may calculate the perpendicular object length H easily since it is the difference between the moving distance of the sensor 6a and the moving distance of the sensor 6b.

The calculator 10 (distance calculator) calculates a candidate object length X on the basis of the parallel object length L and the perpendicular object length H by means of trigonometry. For example, X is equal to the square root of the sum of the squares of L and H. Alternatively, X equals L/cos θ1 where the tangent of θ1 is equal to H/L.

In this modified embodiment, although the first measurement line is not arranged in the same straight line with the second measurement line, the distance calculator can calculate a candidate object length X on the basis of the parallel and perpendicular object lengths L and H.

This modified embodiment can be used such that one of the first and second sensors in one pair is moved (with or without the leg to which the moved sensor is attached) whereas the other in this pair is fixed, and a plurality of oblique candidate object lengths between a fixed object position and a variable object position is calculated. Then, the maximum object length is selected from among all the candidate object lengths.

This modified embodiment can be also used such that a plurality of oblique candidate object lengths between a first object position and a plurality of second object positions are calculated on the basis of a first gap distance and a plurality of second gap distances. Then, further oblique candidate object lengths between another first object position and a plurality of second object positions are calculated on the basis of another first gap distance and a plurality of second gap distances, and this calculation is repeated with reference to other first gap distances. Lastly, the maximum object length is selected from among all the oblique candidate object lengths.

Figure 14:
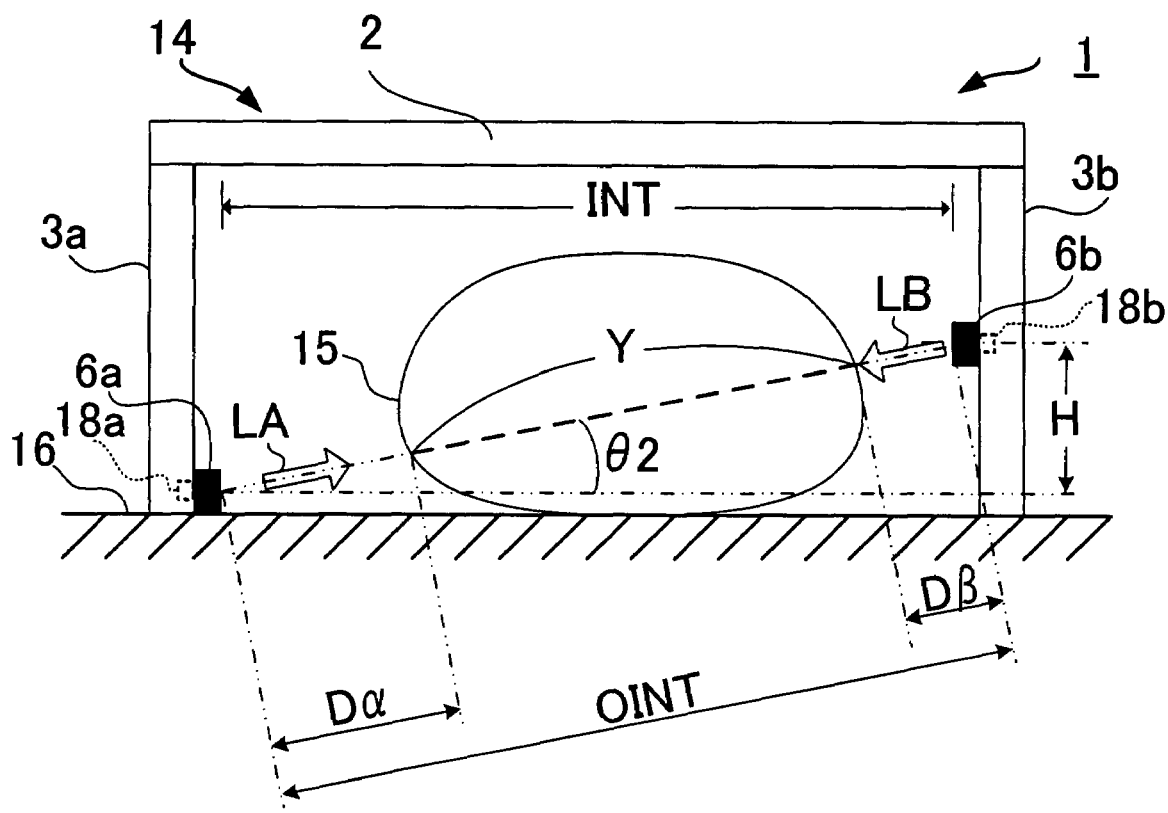
FIG. 14 is a front view of a linear measurement apparatus according to another modified embodiment which has been set with respect to a measured object.

FIG. 14 shows another modified embodiment. It should be noted that the modification in this modified embodiment is also applicable to all of the first and second embodiments and the above-described alternative embodiments, except for that in FIG. 13, although the same reference symbols as in the first embodiment are used in FIG. 14.

In the modified embodiment shown in FIG. 14, angles of the first and second sensors are adjusted, so that the first and second sensors measures first and second oblique gap distances Dα and Dβ, respectively. An oblique candidate object length Y is measured on the basis the first oblique gap distance Dα and a second oblique gap distance Dβ of which the first and second oblique measurement lines are identical to each other. As shown in FIG. 14, let us assume that a second sensor 6B is located at an upper position, whereas a first sensor 6b is located at a lower position. The illustrated sensors 6a and 6b are employed for sampling first and second oblique gap distances Dα and Dβ in order to determine an oblique candidate object length Y The above-mentioned horizontal distance-interval INT between the sensors 6a and 6b is already known. The elevational difference H between the sensors 6a and 6b is already known or may be calculated easily as described in conjunction with the embodiment shown in FIG. 13.

In the microcomputer 8, the calculator 10 serves as an angle calculator, i.e., angle calculating means for calculating the angle θ2 of the straight line between the first and second sensors 6a and 6b with respect to the connection part 2 of the frame 14 on the basis of the horizontal distance-interval INT and the elevational difference H. θ2 is the arctangent of H/INT.

The modified embodiment includes at least one pair of sensor angle adjusters 18a and 18b each attached to the sensors 6a or 6b. Each sensor angle adjuster includes a motor, a solenoid, or other suitable type of actuator for adjusting the angle of the measurement line of the corresponding sensor. In the microcomputer 8, the controller 9 controls or activates the sensor angle adjusters 18a and 18b, on the basis of the calculated angle θ2, so that the first measurement line in which the oblique first gap distance Dα is measured by the first sensor 6a is identical to the second measurement line in which the second oblique gap distance Dβ is measured by the second sensor 6b.

In this embodiment, the sensor angle adjusters 18a and 18b adjust the angle of each of the first and second sensors 6a and 6b for aligning the directions of the first and second gap distances Dα and Dβ. Therefore, the calculator 10 (distance calculator) can precisely calculate an oblique candidate object length Y between the first and second object positions in the same oblique line between the first and second sensors 6a and 6b on the basis of the oblique gap distances Dα and Dβ, the calculated angle θ2, and the constant horizontal distance-interval INT. That is to say, Y equals OINT minus Dα minus Dβ, where OINT is INT/cos θ2.

This modified embodiment can be used such that one of the first and second sensors in one pair is moved (with or without the leg to which the moved sensor is attached), whereas the other in this pair is fixed, and a plurality of oblique candidate object lengths along a straight oblique line between a fixed sensor position and a variable sensor position are calculated. Then, the maximum object length is selected from among all the oblique candidate object lengths.

This modified embodiment can be also used such that a plurality of oblique candidate object lengths along a straight oblique line between a first sensor position and a plurality of second sensor positions are calculated on the basis of a variable first oblique gap distance and a plurality of second oblique gap distances. Then, further candidate object lengths along a straight oblique line between another first sensor position and a plurality of second sensor positions are calculated on the basis of another variable first oblique gap distance and a plurality of second oblique gap distances, and this calculation is repeated with reference to other first sensor positions. Lastly, the maximum oblique object length is selected from among all the oblique candidate object lengths.

Third Embodiment

Figure 15:
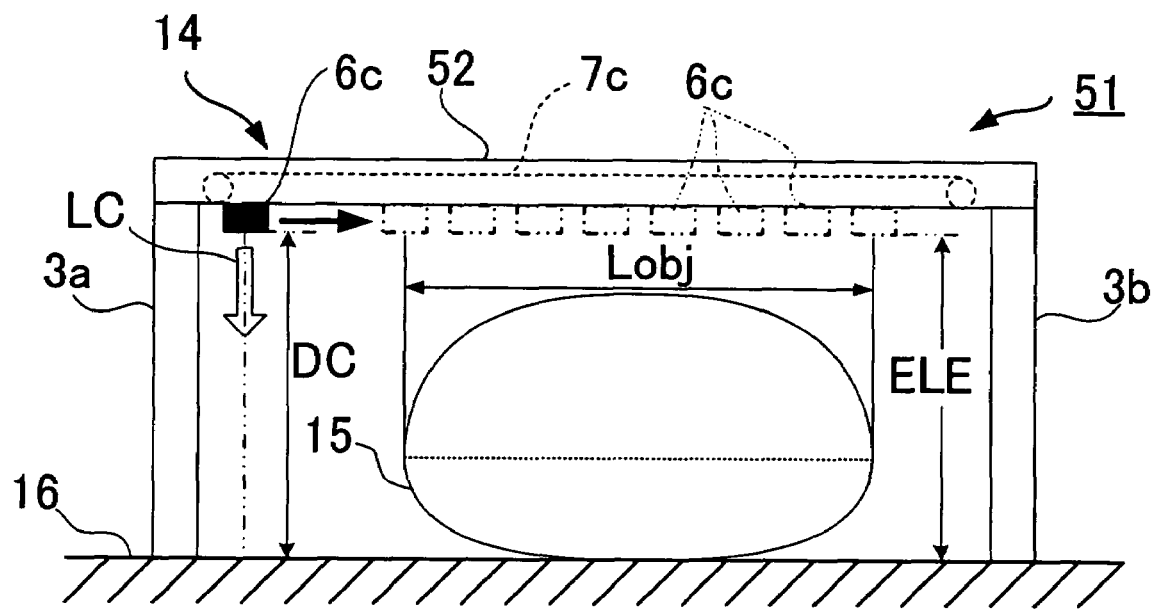
FIG. 15 is a front view of a linear measurement apparatus according to a third embodiment.
Figure 16:
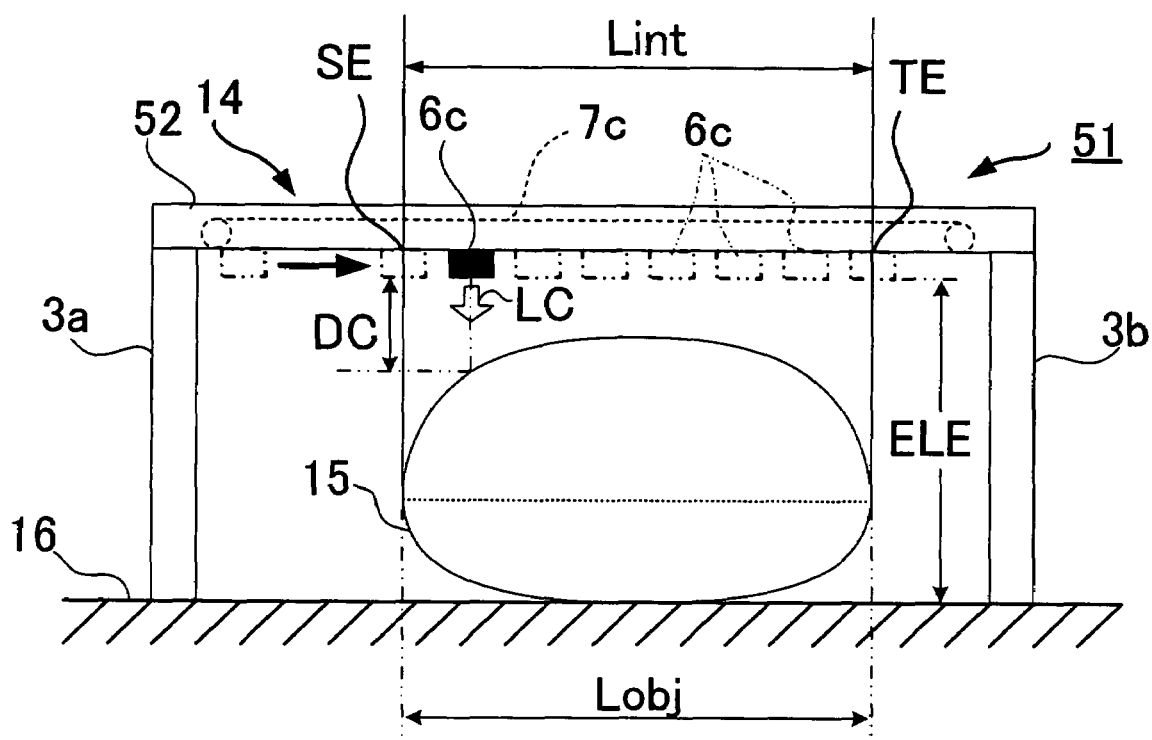
FIG. 16 is a front view of the linear measurement apparatus in FIG. 15 in which a sensor is in another position.

As shown in FIGS. 15 and 16, a linear measurement apparatus 51 according to a third embodiment of the present invention includes a supporting member, i.e., portable frame 14 that is substantially the same as in the first embodiment. The linear measurement apparatus 51 also includes a measuring unit for estimating the object length Lobj shown in FIG. 15. The measuring unit of this embodiment includes a single noncontact distance measuring sensor 6c movably supported at the horizontally extended connection part 52 of the frame 14. The type of sensor employed is the same as that in the first embodiment. Thus, it has a light emitter for emitting a light beam (such as for example, but not limited to, an infrared light beam) vertically downward and a light receiver for receiving the light reflected from whatever in front of the sensor, such as the measured object 15 or the bed 16, and for generating a signal corresponding to the distance from the corresponding sensor to whatever in front of the sensor. Thus, the sensor 6c measures the gap distance between the sensor 6c and a measured position in a measurement line extending vertically. In FIGS. 15 and 16, arrow LC represents the light beam downwardly emitted from the sensor 6c.

A driving mechanism 7c is located at the connection part 52 for moving the sensor 6c to an extent horizontally with respect to the frame 14. The type of the driving mechanism employed is the same as that in the first embodiment. By means of the driving mechanism 7c, the sensor 6c is shifted horizontally along the connection part 52, as depicted by phantom lines in FIGS. 15 and 16.

During the period in which the sensor 6c is moved horizontally, the single sensor 6c measures a plurality of gap distances DC to a plurality of measured positions in a plurality of parallel vertical measurement lines on the same vertical plane, each gap distance being between a sensor position of the sensor 6c and a measured position on the bed 16 or the measured object 15.

In the state shown in FIG. 15, the sensor 6c measures a gap distance DC between the sensor 6c and the bed 16 with which a vertical measurement line (path of the light beam from the sensor 6c) intersects. The gap distance DC in this state is almost equal to a reference elevation ELE of the sensor 6c that is the vertical distance between the sensor 6c and the bottom of the legs 3a and 3b. On the other hand, in the state shown in FIG. 16, the sensor 6c measures another gap distance DC between the sensor 6c and an object position of the measured object 15 with which another vertical measurement line (path of the light beam from the sensor 6c) intersects.

As will be understood from FIG. 15, the gap distance DC measured is very large when the sensor 6c is not located above the measured object 15. In contrast, as shown in FIG. 16, the gap distance DC measured is small when the sensor 6c is located above the measured object 15. Therefore, both ends SE and TE of the measured object 15 can be detected on the basis of comparison of the amount of the gap distance DC with at least one threshold, and the length Lobj of the measured object 15 between both ends SE and TE of the measured object can be estimated. This is a generic principle of the maximum length measurement achieved by the apparatus 51. The precision of estimation of the object length Lobj will be improved when the horizontal distance-interval of the vertical measurement lines is reduced and the number of measured gap distances is increased.

Figure 17:
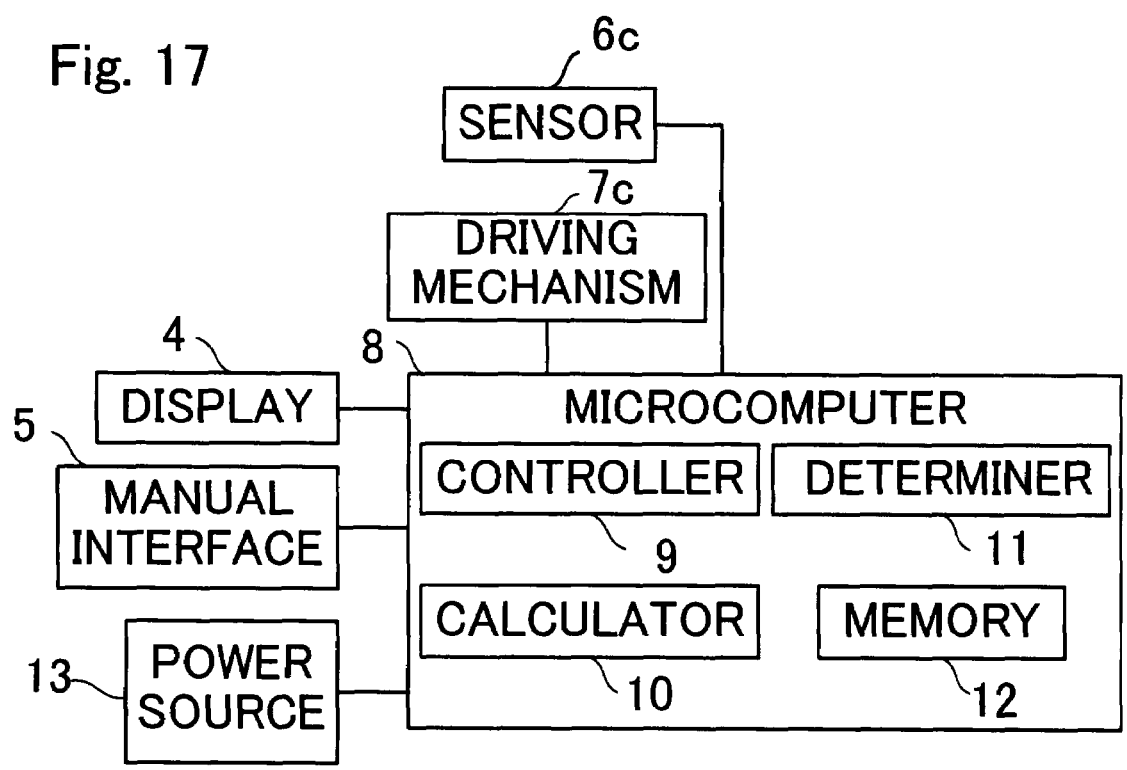
FIG. 17 is a block diagram showing elements of the linear measurement apparatus in FIG. 16.

With reference to the block diagram of FIG. 17, the electrical structure of linear measurement apparatus 51 will be described. The block diagram of FIG. 17 is similar to FIG. 5 of the first embodiment, but in FIG. 17 the sensor 6c and the driving mechanism 7c are connected with the microcomputer 8 instead of the sensors 6a and 6b and the driving mechanisms 7a.

Instead of control of the sensors 6a and 6b for distance measurement and the driving mechanisms 7a for moving the sensors 6a and 6b, the controller 9 controls the sensor 6c for measuring the distances DC and controls the driving mechanism 7c for moving the sensor 6c.

The calculator 10 serves as a length calculator, i.e., length calculating means for calculating the object length Lobj between both ends, namely the first and second ends of the measured object 15.

The determiner 11 serves as a measured-object-end detector, i.e., measured-object-end detecting means for detecting the first end and the second end of the measured object 15 on the basis of an amount of each of the plurality of gap distances DC.

The memory 12 stores in advance various data such as default values, system settings, and arithmetic expressions. Furthermore, the memory 12 stores in advance thresholds for determining the first end SE and the second end TE of the measured object 15.

Figure 18A:
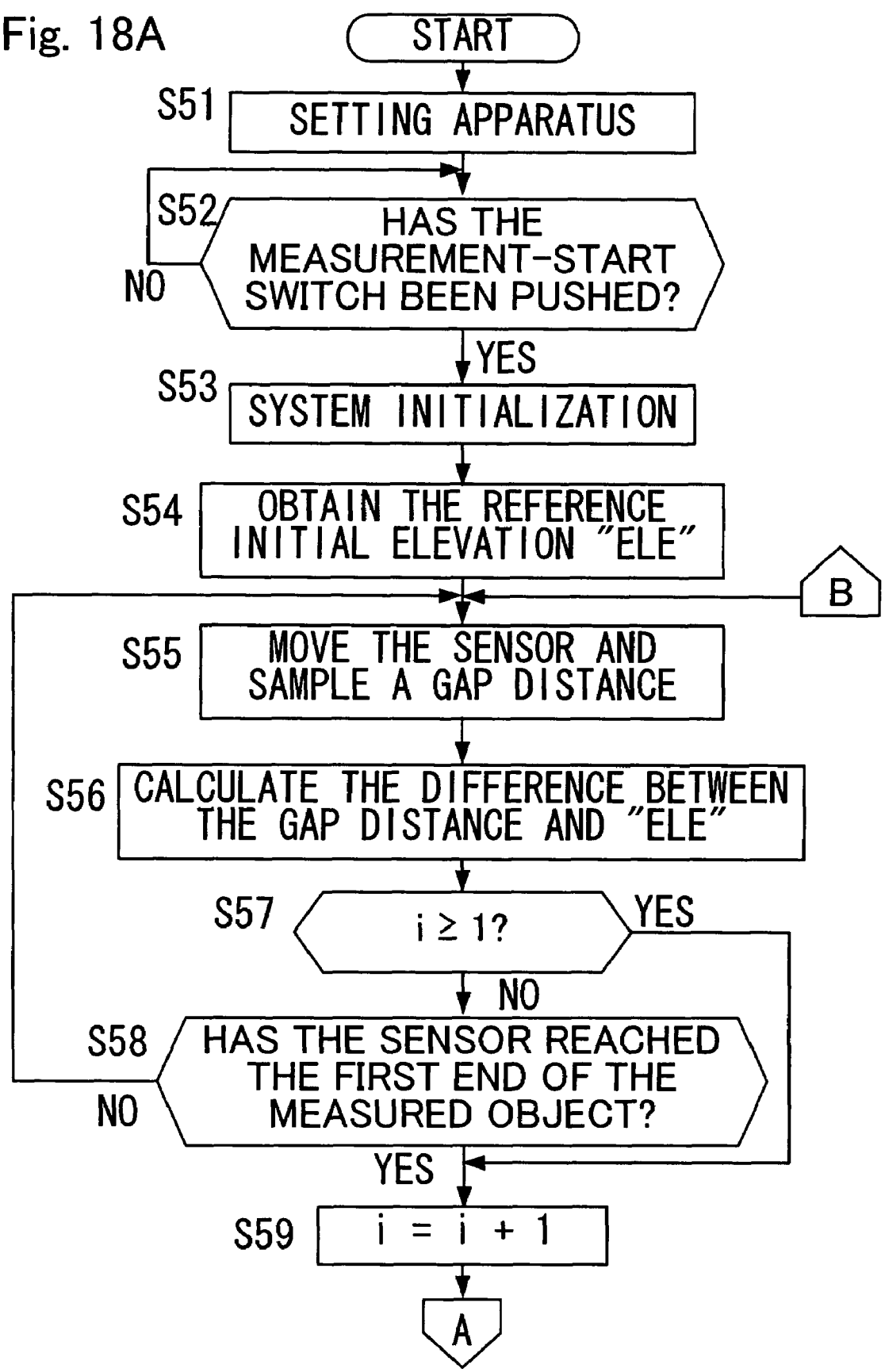
FIGS. 18A and 18B form a flowchart showing use and operations of the linear measurement apparatus in FIG. 16.
Figure 18B:
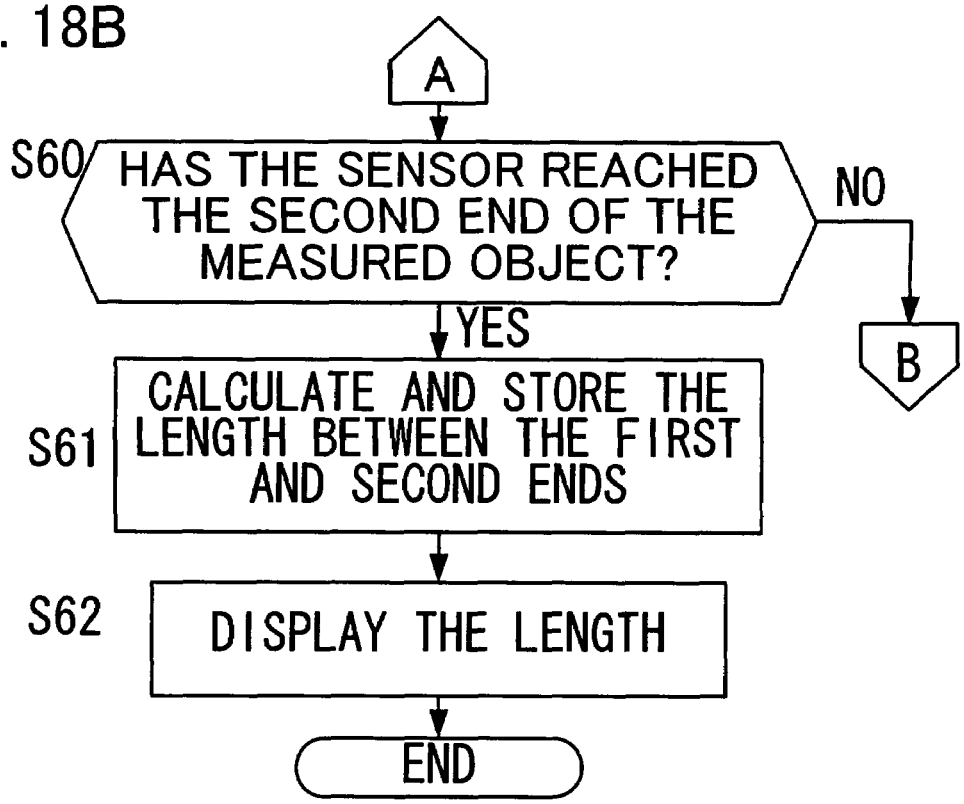

With reference to the flowchart shown in FIGS. 18A and 18B, use and operations of the linear measurement apparatus 51 will be described in more detail. Steps executed by the microcomputer 8 within the operations in the flowchart correspond to the computer program or an element of the computer program stored in the memory 12 or another memory or storage device. Steps S51, S52, and S53 after turning on power are the same as steps S1, S2, and S3 in FIG. 5 of the first embodiment, and they are therefore not described in detail. However, at step S53, the microcomputer 8 initializes the position of the sensor 6c instead of the positions of the sensors 6a and 6b. In addition, a counter is functionally or physically provided in the microcomputer 8 for counting the number of times of sampling of gap distances DC when the sensor 6c is located above the measured object 15. The counter number "i" is reset at zero (default value) at step S53 for system initialization.

At step S54, the microcomputer 8 serves as the controller 9 to activate sensor 6c, and therefore, the sensor 6c measures the initial vertical gap distance between the sensor 6c and the bed 16. The microcomputer 8 thus obtains this initial vertical gap distance and stores it as a reference initial elevation ELE of the sensor 6c in the memory 12.

At step S55, the microcomputer 8 serves as the controller 9 to control the driving mechanism 7c for moving the sensor 6c at a constant speed. As a result, the sensor 6c measures or samples one of the gap distances DC. As will be understood from the flowchart, whenever the process returns to step S55, the sensor 6c is moved and activated to measure the next gap distance DC, so that the measured object 15 is scanned at regular sampling time intervals.

At step S56, the calculator 10 calculates the difference between the last measured gap distance and the reference initial elevation ELE. At step S57, the microcomputer 8 serves as the determiner 11 for determining whether or not the vertical measurement line of the sensor 6c is located above the measured object 15. This determination is achieved by determining whether or not the above-mentioned counter number "i" is equal to or greater than one.

If "i" is less than one (the sensor 6c is not above the measured object 15), the process proceeds to step S58 where the determiner 11 serves as the measured-object-end detector for determining whether or not the measurement line of the sensor 6c has reached the first end (start end) SE of the measured object 15. This determination is achieved by comparing the difference calculated at step S56 with a threshold P stored in the memory 12. If the difference is greater than P, the measurement line of the sensor 6c has reached the start end SE. This determination is the same as that in which the determiner 11 determines that the sensor 6c has reached the start end SE of the measured object 15 when the sensor 6c measures a gap distance DC that is less than another threshold.

If the determination at step S58 is negative (the difference is not greater than P), the process returns to step S55 where the next gap distance DC is sampled. If the determination at step S58 is affirmative (the difference is greater than P), the process proceeds to step S59 where the microcomputer 8 increments the counter number "i" by one.

If the counter number "i" is equal to or greater than one, the determination at step S57 is affirmative and the process proceeds directly to step S59 (not via step S58) since the system already knows that the sensor 6c is traveling above the measured object 15.

At step S60, the determiner 11 serves as the measured-object-end detector for determining whether or not the measurement line of the sensor 6c has reached the second end (termination end) TE of the measured object 15. This determination is achieved by comparing the difference calculated at step S56 with a threshold Q stored in the memory 12. The threshold Q may be or may be not the same as the above-mentioned threshold P. If the difference is equal to or less than Q, the measurement line of the sensor 6c has reached the termination end TE. This determination is the same as that in which the determiner 11 determines that the sensor 6c has reached the termination end TE of the measured object 15 when the sensor 6c measures a gap distance DC that is greater than another threshold.

If the determination at step S60 is negative (the difference is greater than Q), the process returns to step S55 where the next gap distance DC is sampled since the sensor 6c is still traveling above the measured object 15.

If the determination at step S60 is affirmative (the difference is not greater than Q), the process proceeds to step S61 where the controller 9 serves as a measurement terminator, i.e., measurement terminating means and terminates the sensor 6c measuring the gap distance and the driving mechanism 7c moving the sensor 6c. Furthermore, the microcomputer 8 holds the current number "i" of the sampling counter, and then on the basis of this number, the calculator 10 serves as the length calculator and calculates an interval length Lint (in FIG. 16) between the sensor position at which the first end SE is detected and the sensor position at which the second end TE is detected. The interval length Lint equals the object length Lobj between the first end SE and the second end TE. The calculation of the interval length Lint is achieved by multiplying the sampling distance-interval by the counter number "i", in which the sampling distance-interval is the sampling period-interval multiplied by the traveling speed of the sensor 6c. The calculator 10 stores the interval length Lint in the memory 12.

At step S62, the microcomputer 8 acts as a display controller for making the display 4 show the value of the interval length Lint (object length Lobj) stored in the memory 12. The microcomputer 8 controls the display 4 such that the display holds the displayed length for a period of time. Since the display holds the displayed object length at least temporarily, the operator can easily confirm the displayed value after completion of measurement, and it is possible to avoid change of the displayed image even if the sensors are moved accidentally after completion of measurement.

The interval length Lint finally stored in the memory 12 and held in the display 4 is the object length Lobj of the measured object 15. After step S62, the process ends.

In the above-described third embodiment, the interval length Lint is calculated on the basis of the sampling counter number "i". However, it is not intended to limit the present invention to this embodiment. In an alternative embodiment, a distance encoder (not shown) may be incorporated in the driving mechanism 7c for measuring the interval length Lint. The distance encoder starts measuring the length when the determiner 11 informs the encoder that the sensor 6c has reached the first end SE. The distance encoder terminates measuring the length Lint when the determiner 11 informs the encoder that the sensor 6c has reached the second end TE.

The above-mentioned initial vertical gap distance need not necessarily be measured in practice since the reference initial elevation ELE is the vertical distance between the sensor 6c and the bottom of the legs 3a and 3b. Therefore, the reference initial elevation ELE may be stored in the memory 12 in advance.

In the above-described third embodiment, the first and second ends are specified on the basis of the gap distances DC measured. However, in an alternative embodiment, the determiner 11 (measured-object-end detector) may determine that the sensor 6c has reached the first end SE when the sensor 6c outputs an error signal, and may determine that the sensor 6c has reached the second end TE when the sensor 6c outputs an error signal again. This alternative embodiment is advantageous in a situation in which there is no suitable reference horizontal plane, to which the initial vertical gap distance can be measured from the sensor, at each side of the measured object 15 within the movable range of the sensor 6c. In accordance with the alternative embodiment, the reference initial elevation ELE and the thresholds can be excluded from use.

Figure 19:
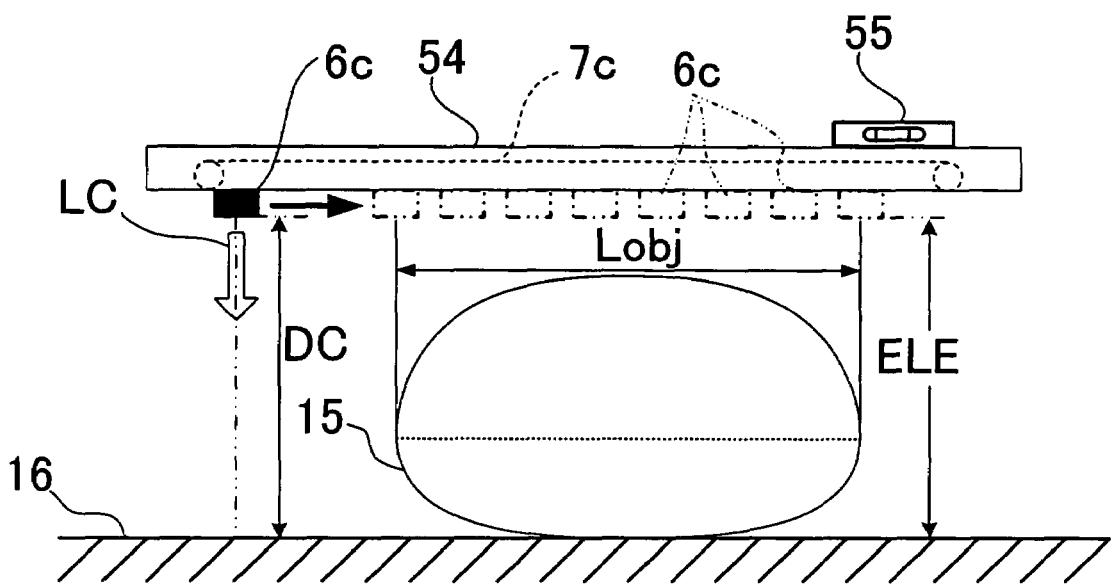
FIG. 19 is a front view of a linear measurement apparatus according to another alternative embodiment.

The above-described linear measurement apparatus 51 includes the frame 14 as a supporting member for supporting the sensor. However, it is not intended to limit the present invention to the embodiment. For example, in an alternative embodiment shown in FIG. 19, the legs 3a and 3b may be excluded, and a straight bar 54 corresponding to only the connection part 52 may be used as a supporting member for supporting the sensor. Preferably, the bar 54 can be provided with a level meter 55 (e.g., a spirit level), an angle sensor, or any other suitable tool for facilitating the operator to maintain the bar horizontal.

In another alternative embodiment (not shown), the sensor 6c may be moved manually by the operator with respect to the frame 14 while the sensor samples the gap distances DC at regular sampling distance-intervals.

Figure 20:
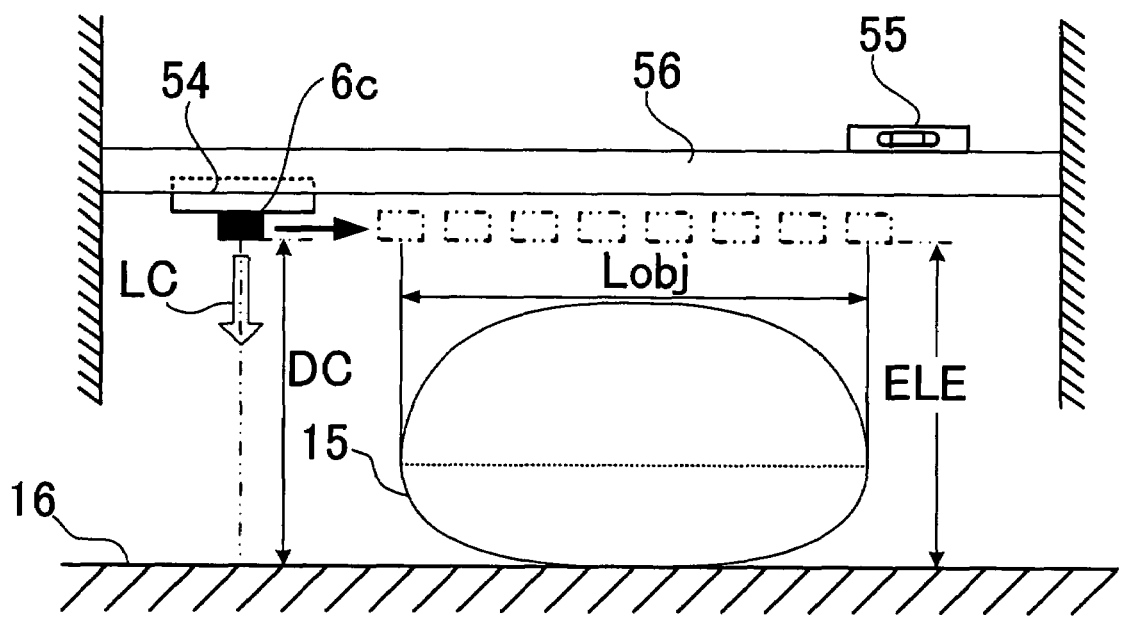
FIG. 20 is a front view of a linear measurement apparatus according to a further alternative embodiment.

In another alternative embodiment shown in FIG. 20, although the sensor 6c is fixed to the straight bar 54, the sensor 6c can be moved along with the straight bar 54 in a group with respect to the measured object 15, so that the single sensor 6c can measure the plurality of gap distances DC. The straight bar 54 with the sensor 6c may be moved manually by the operator. A horizontal guide 56 is provided for guiding horizontal movement of the bar 54 with respect to the measured object 15 in order to facilitate sliding of the bar 54.

In the above-described third embodiment, the object length Lobj between the first end SE and the second end TE of the measured object 15 is considered as the interval length Lint between the sensor position at which the first end SE is detected and the sensor position at which the second end TE is detected. However, if the connection part 52 is inclined, the interval length Lint is not equal to the object length Lobj. In this case, the object length Lobj is calculated by means of trigonometry on the basis of the interval length Lint and the elevational difference between the between the sensor position at which the first end SE is detected and the sensor position at which the second end TE is detected.

Figure 21:
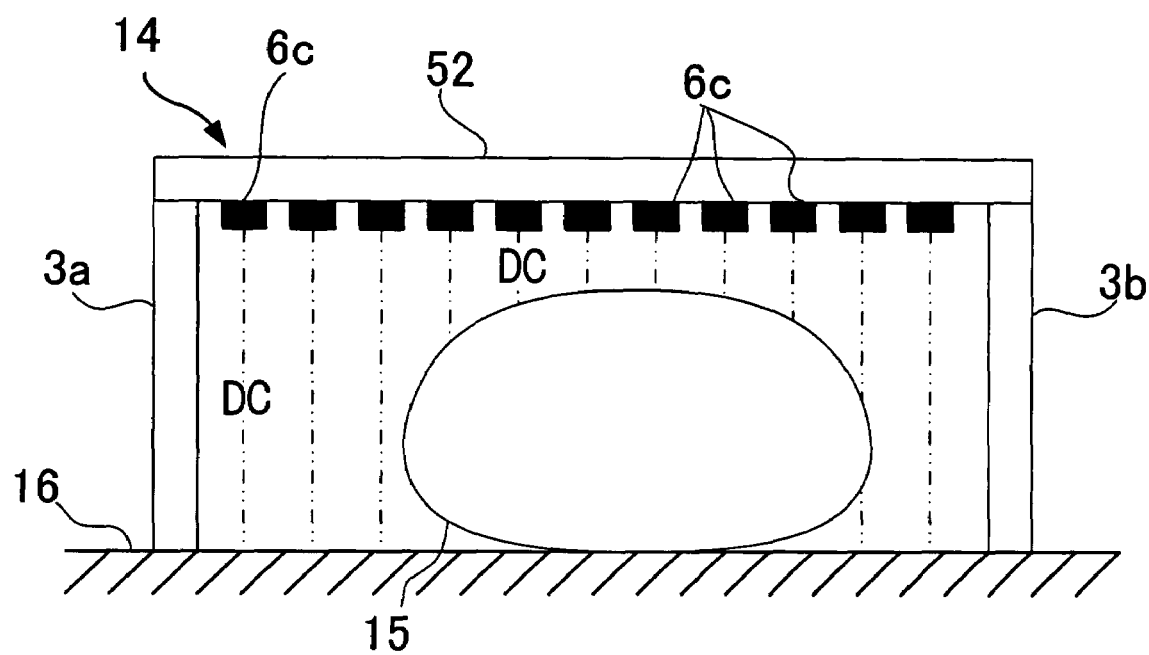
FIG. 21 is a front view of a linear measurement apparatus according to a further alternative embodiment.

In another alternative embodiment shown in FIG. 21, the measuring unit includes a plurality of the noncontact distance measuring sensors 6c fixedly supported at the connection part 52 of the frame 14. The sensors 6c are spaced equally with respect to each other and measure a plurality of gap distances DC to a plurality of measured positions in a plurality of vertical parallel measurement lines, respectively. In this embodiment, the apparatus can be manufactured easily since the sensors 6a are fixed to the frame 14 and the above-described driving mechanism 7c is excluded. In addition, the use of the apparatus is simplified since the automatic or manual movement of the sensor 6c (with or without the supporting member) is unnecessary. The precision of estimation of the object length Lobj will be improved when the number of the sensors is increased.

Modifications

Figure 22:
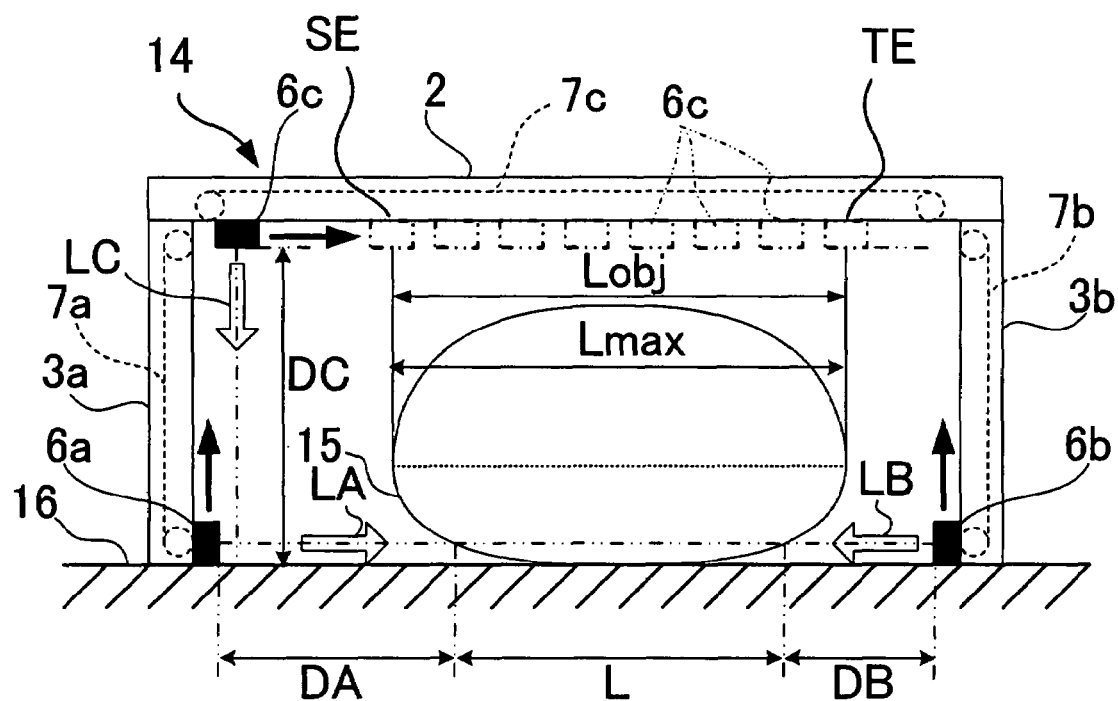
FIG. 22 is a front view of a linear measurement apparatus according to a modification into which the first embodiment shown in FIGS. 1 through 4 and the third embodiment shown in FIGS. 15 through 17 are combined.

FIG. 22 shows a modification in which the first embodiment shown in FIGS. 1 through 4 and the third embodiment shown in FIGS. 15 through 17 are combined. This modification includes a measuring unit including one pair of movable sensors (namely the first and second sensors 6a and 6b) supported at the legs 3a and 3b of the frame 14 for measuring first and second gap distances DA and DB; and an additional measuring unit including a third sensor 6c movably supported at connection part 2 of the frame 14 for measuring third gap distances DC.

Figure 23:
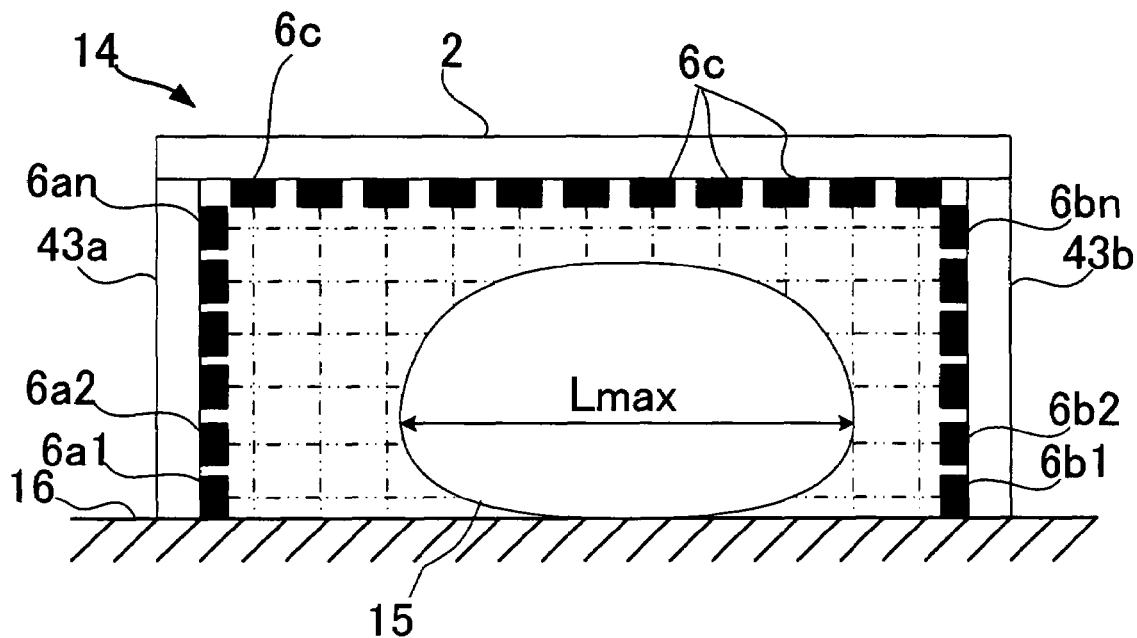
FIG. 23 is a front view of a linear measurement apparatus according to another modification into which the second embodiment shown in FIG. 10 and the alternative embodiment shown in FIG. 21 are combined.

FIG. 23 shows another modification into which the second embodiment shown in FIG. 10 and the alternative embodiment shown in FIG. 21 are combined. This modification includes a measuring unit including a plurality of pairs of fixed sensors (namely the first and second sensors 6a and 6b) supported at the legs 3a and 3b of the frame 14 for measuring first and second gap distances DA and DB; and an additional measuring unit including a plurality of third sensors 6c fixedly supported at connection part 2 of the frame 14 for measuring third gap distances DC.

The calculator 10 in the microcomputer 8 for the modifications in FIGS. 22 and 23 serves as a distance calculator for calculating a plurality of candidate object lengths L in a manner similar to that in the first or second embodiment. The determiner 11 serves as a measured-object-end detector for detecting a first end SE and a third end TE of the measured object 15 on the basis of the plurality of third gap distances DC in a manner similar to that in the third embodiment. The calculator 10 also serves as a length calculator for calculating an object length Lobj in a manner similar to that in the third embodiment. The determiner 11 also serves as a maximum selector that selects the maximum object length Lmax from among the object length Lobj and the plurality of candidate object lengths L, instead of or in addition to selecting a maximum from among the plurality of candidate object lengths L. Alternatively, the maximum selector may select the maximum object length Lmax from among the plurality of candidate object lengths L, and may obtain a final measurement result by averaging the maximum object length Lmax and the object length Lobj. In either case, a more reliable result can be obtained.

Figure 24:
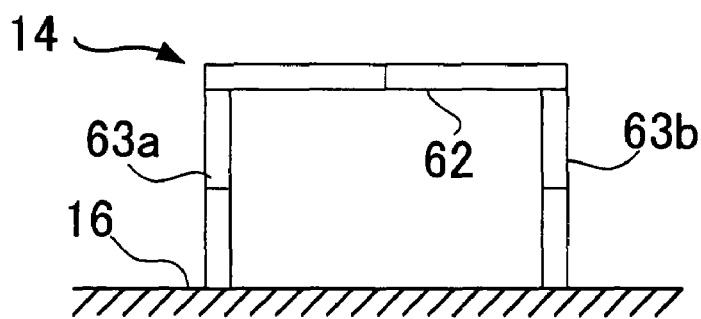
FIG. 24 is a front view of a linear measurement apparatus according to another modification.
Figure 25:
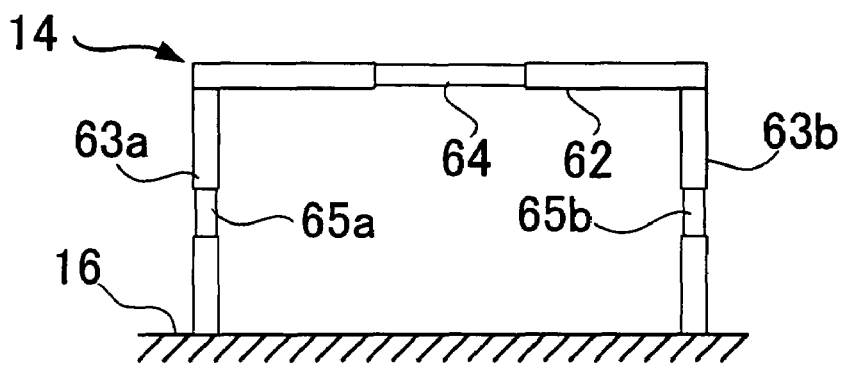
FIG. 25 is a front view of the linear measurement apparatus in FIG. 24 in another situation.

FIGS. 24 and 25 show another modification applicable to all of the above-described embodiments and modifications. This modification has a variant of the frame 14, and therefore illustration of other elements is omitted in FIGS. 24 and 25.

More specifically, the frame 14 includes a frame-size adjustment mechanism (supporting-member-size adjustment mechanism) for permitting the size of the frame (supporting member) to be adjusted. Accordingly, the frame 14 has a pair of extendable legs 63a and 63b vertically standing on the bed 16 and an extendable connection part 62 of which both ends are connected to the legs 63a and 63b. The horizontal connection part 62 has a center shaft 64 and a pair of sheaths slidably mounted on the center shaft 64, so that the connection part 62 is extendable. Each leg 63a or 63b has a center shaft 65a or 65b and a pair of sheaths slidably mounted on the center shaft, so that the legs are extendable.

By virtue of the frame-size adjustment mechanism, objects of various sizes can be measured. Especially, with the extendable connection part 62 being applied in the above-described first or second embodiment, the distance-interval between the first and second sensors 6a and 6b in a direction parallel to the first and second measurement lines is adjustable. With the extendable legs 63a and 63b applied in the first or second embodiment, the range of movement of the sensors 6a and 6b is adjustable. On the other hand, with the extendable connection part 62 being applied in the above-described third embodiment, the range of movement of the sensor 6c is adjustable.

Although in the illustrated embodiment the legs 63a and 63b and the connection part 62 are extendable, it is contemplated that only legs or the connection part may be extendable. It is also contemplated that in the embodiment shown in FIG. 20 the straight bar 54 (supporting member) may be modified to be extendable.

Figure 26:
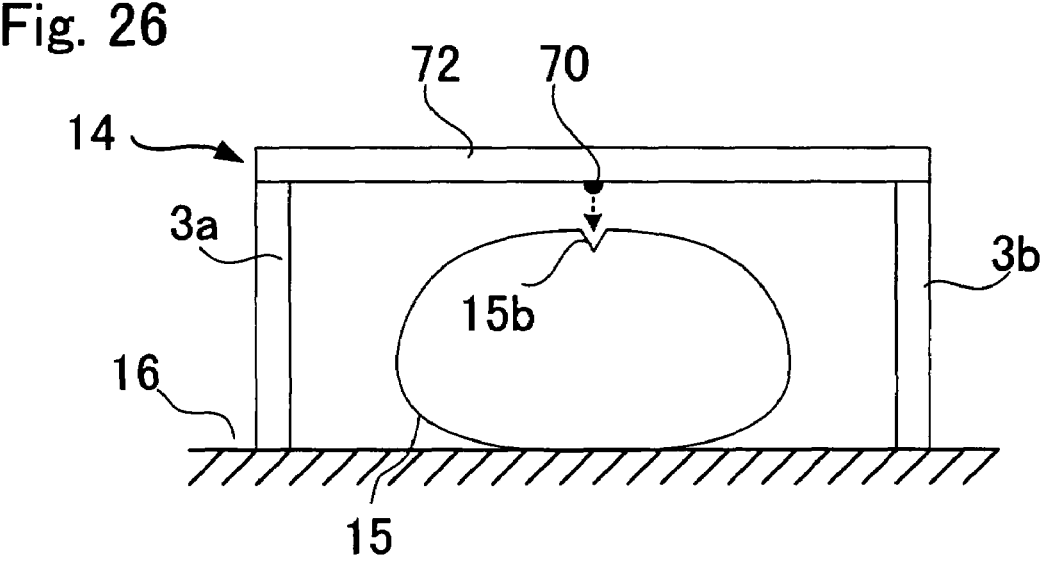
FIG. 26 is a front view of a linear measurement apparatus according to another modification.
Figure 27:
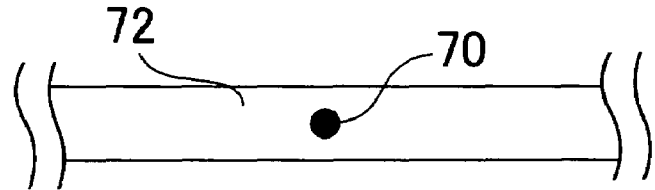
FIG. 27 is a bottom view of a linear measurement apparatus in FIG. 27.

FIGS. 26 and 27 show another modification applicable to all of the above-described embodiments and modifications. Illustration of sensors is omitted in FIGS. 26 and 27. In this modification, a reference light emitter 70 is located at the connection part 72 frame or the supporting member (e.g., the straight bar 54) for irradiating reference light onto the measured object 15 in order to facilitate deployment, i.e., positioning of the linear measurement apparatus with respect to a reference position 15b of the measured object 15. The reference light is, for example, but not limited to, a laser pointer that emits a narrow beam. If it is desirable to measure the length in a specific cross section of the measured object 15 in which the reference position 15b is situated, this modification is advantageous for reliable measurement.

Additionally, if the reference light emitter 70 is located at the center position of the connection part 72, the apparatus can be deployed such that the measured object 15 is centered between the legs 3a and 3b. This is advantageous for the first and second embodiments in which the first and second sensors 6a and 6b are arranged on opposite sides of the measured object 25 when the measured object 15 is very small. If the measured object 15 is very small and too far from a sensor, there is likelihood that only a small amount of light reflected at the measured object 15 reaches the sensor so that the sensor cannot measure the gap distance. However, according to this modification, centering the measured object 15 between the legs 3a and 3b can reduce such an adverse effect. The reference light emitter 70 may be slidably attached to the connection part 72 slidably along the longitudinal direction of the connection part 72.

Figure 28:
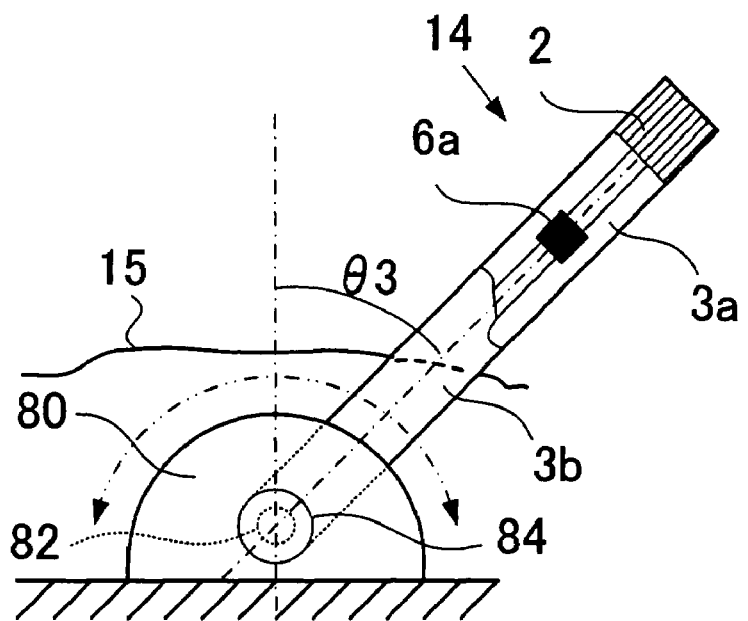
FIG. 28 is a side view of a linear measurement apparatus according to another modification.

FIG. 28 is a side view of another modification applicable to all of the above-described embodiments and modifications. This modification includes a frame-inclination adjustment mechanism (supporting-member-inclination adjustment mechanism) for permitting an inclination of the frame (supporting member) 14 to be adjusted with respect to the measured object 15. More specifically, the lower portions of the respective legs 3a and 3b of the frame 14 are pivotally attached to respective rotation bases 80 so that the frame 14 can be swung about coaxially aligned shafts 82 within a predetermined angular range. Setscrews 84 are tightened to lock the legs 3a and 3b to the rotation bases 80 in a selected angle, e.g., θ3. In this modification, measurements can be made along various planes of inclination.

The above-described embodiments with one or more automatically or manually movable sensors (with or without the supporting member) can be modified as follows. The manual interface 5 has means by which the operator instructs to start and stop the sensor 6c or the pair of sensors 6a and 6b, e.g., a measurement-start switch and a measurement-stop switch. The controller 9 may serve as a measurement starter and a measurement terminator: the measurement starter starts the sensor 6c or sensors 6a and 6b measuring the corresponding gap distances when the operator has instructed to start them, and the measurement terminator terminates the sensor or sensors measuring the corresponding gap distances when the operator has instructed to stop them. With respect to the automatically movable sensor or sensors, the measurement starter additionally starts the driving mechanism 7c or the driving mechanisms 7a and 7b moving the sensor 6c or sensors 6a and 6b when the operator has instructed to start them, and the measurement terminator additionally terminates the driving mechanism or the driving mechanisms moving the sensor or sensors when the operator has instructed to start them. With such a structure, the operator can instruct to start and stop the measurements with the sensor or sensors at optional positions during movement of the sensor or sensors, so that the operator can determine the measurement range freely. Concerning the embodiments with a plurality of sensors, each sensor may be started or stopped independently or simultaneously.

Figure 29:
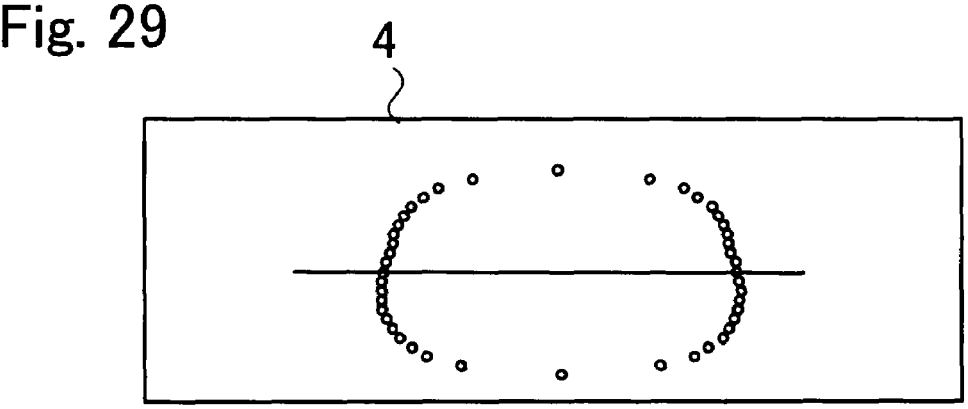
FIG. 29 is an illustration showing a two-dimensional image displayed on a display according to the first and second embodiments.
Figure 30:
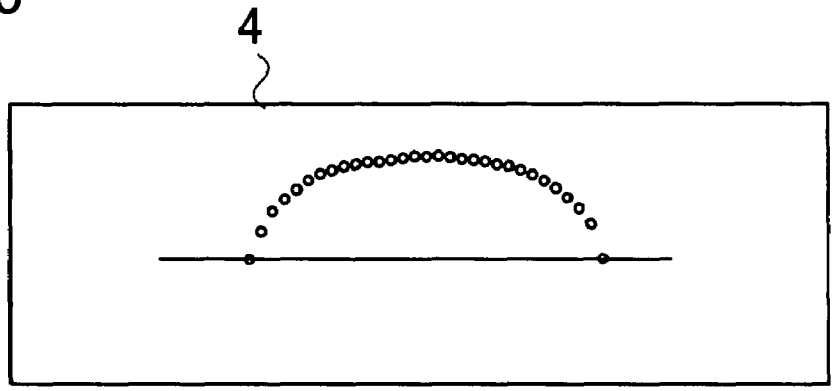
FIG. 30 is an illustration showing a two-dimensional image displayed on a display according to the third embodiment.

FIGS. 29 and FIG. 30 shows two-dimensional images displayed on the display 4 according to the embodiments. FIG. 29 corresponds to the first and second embodiments and their modifications whereas FIG. 30 corresponds to the third embodiment and its modifications. The display 4 is, for example, but is not limited to, a liquid crystal display or a dot matrix display. After displaying the measurement result of the length, the microcomputer 8, as a display controller, makes the display 4 display measured positions as a two-dimensional image as shown in FIG. 29 or 30. Therefore, operators can easily recognize quickly the cross section, i.e., outline of the measured object 15 at a glance although the cross section is complicated.

For displaying measured positions, concerning the first and second embodiments and their modifications, the microcomputer 8 obtains coordinates of each of first object positions and the second object positions. The X coordinate of each first object position is the sum of the corresponding first gap distance and the known X coordinate of the first sensor 6a. The X coordinate of each second object position is the known X coordinate of the second sensor 6b minus the corresponding second gap distance. The Y coordinate of each object position is the Y coordinate of the sensor which has sampled the object position. Based on determination of XY coordinates of the object positions, the microcomputer 8 controls the display 4 such that a cross section of the measured object defined by the first object positions and the second object positions is displayed as a two-dimensional image.

For displaying measured positions, concerning the third embodiment and its modifications, the microcomputer 8 obtains coordinates of each of measured positions from the first end SE to the second end TE of the measured object 15. The X coordinate of each measured position is the coordinate of the sensor which has sampled the measured position. The Y coordinate of each measured position is the known Y coordinate of the sensor 6c minus the corresponding gap distance. Based on determination of XY coordinates of the measured positions, the microcomputer 8 controls the display 4 so that the measured positions are displayed as a two-dimensional image.

While in the above-described embodiments the display 4 is used as an output device to which the measurement result is output, the apparatus may outputs the measurement result in any other suitable manner. For example, the apparatus may include a printer for printing out the measurement result in response to output signals from the microcomputer 8. The apparatus may send and/or store measurement result signals indicating the measurement result to an outside device.

While the present invention has been particularly shown and described with references to preferred embodiments thereof, it will be understood by those skilled in the art that various changes in form and details may be made therein without departing from the spirit and scope of the invention as defined by the claims. Such variations, alterations, and modifications are intended to be encompassed in the scope of the present invention.

What is claimed is:

1. A linear measurement apparatus comprising:
   a frame which can be disposed around a measured object;
   a measuring unit comprising at least one pair of noncontact distance measuring sensors supported at the frame, the pair of noncontact distance measuring sensors comprising a first noncontact distance measuring sensor and a second noncontact distance measuring sensor, each sensor emitting light, receiving the light reflected from a measured object, and generating a signal corresponding to a distance from the corresponding sensor to the measured object, the first and second sensors being aligned on opposite sides of the measured object within the frame, the first sensor measuring a first gap distance between the first sensor and a first object position on the measured object in a first measurement line, the second sensor measuring a second gap distance between the second sensor and a second object position on the measured object in a second measurement line parallel to or identical to the first measurement line, the measuring unit measuring a plurality of first gap distances to a plurality of first object positions in a plurality of parallel first measurement lines and a plurality of second gap distances to a plurality of second object positions in a plurality of parallel second measurement lines lying on a plane identical to that in which the first measurement lines lie;
   a reference light emitter located at the frame for irradiating reference light onto the measured object in order to facilitate deployment of the linear measurement apparatus with respect to a reference position of the measured object;
   a distance calculator for calculating a plurality of candidate object lengths on the basis of the plurality of first and second gap distances, each candidate object length being a distance between one of the first object positions and one of the second object positions; and
   a maximum selector for selecting a maximum object length from among the plurality of candidate object lengths.

2. The linear measurement apparatus according to claim 1, further comprising driving mechanisms for respectively moving the first and second noncontact distance measuring sensors with respect to the frame, wherein the first sensor measures a plurality of first gap distances to a plurality of first object positions in a plurality of first parallel measurement lines, each first gap distance being between a sensor position of the first sensor and a first object position on the measured object, and wherein the second sensor measures a plurality of second gap distances to a plurality of second object positions in a plurality of second parallel measurement lines, each second gap distance being between a sensor position of the second sensor and a second object position on the measured object.

3. The linear measurement apparatus according to claim 2, further comprising:
   a limit detector for determining whether or not at least one of the first and second noncontact distance measuring sensors has reached a limit of movement of the corresponding sensor; and
   a measurement terminator for terminating the corresponding sensor measuring the corresponding gap distance when the limit detector has detected that the corresponding sensor has reached the limit.

4. The linear measurement apparatus according to claim 1, wherein the pair of noncontact distance measuring sensors are fixedly supported at the frame in such a manner that the first measurement line in which the first gap distance is measured by the first sensor is identical to the second measurement line in which the second gap distance is measured by the second sensor.

5. The linear measurement apparatus according to claim 4, further comprising at least one guide for guiding movement of the frame with respect to the measured object.

6. The linear measurement apparatus according to claim 1, further comprising:
   an end detector for determining whether or not at least one of the first and second noncontact distance measuring sensors has reached an end of the measured object; and
   a measurement terminator for terminating the corresponding sensor measuring the corresponding gap distance when the end detector has detected that the corresponding sensor has reached the end of the measured object.

7. The linear measurement apparatus according to claim 6, wherein the end detector determines that the corresponding sensor has reached the end of the measured object when the corresponding sensor measures a first or second gap distance that is greater than a threshold.

8. The linear measurement apparatus according to claim 1, further comprising:
   a manual interface by which an operator instructs to start and stop the first and second sensors;
   a measurement starter for starting the first and second sensors measuring the first and second gap distances when the operator has instructed to start the 5 first and second sensors; and
   a measurement terminator for terminating the first and second sensors measuring the first and second gap distances when the operator has instructed to stop the first and second sensors.

9. The linear measurement apparatus according to claim 1, wherein the measuring unit comprising a plurality of pairs of the noncontact distance measuring sensors, each pair comprising the first and second noncontact distance measuring sensors fixedly supported at the frame, wherein each of the first sensors measures a first gap distance between the corresponding first sensor and a first object position on the measured object in a first measurement line, and wherein each of the second sensors measures a second gap distance between the corresponding second sensor and a second object position on the measured object in a second measurement line parallel to or identical to the first measurement line.

10. The linear measurement apparatus according to claim 1, wherein the frame is of a shape in which one side is open, the frame having a pair of legs and a connection part connecting the legs, the first and second noncontact distance measuring sensors being supported on the legs, respectively.

11. The linear measurement apparatus according to claim 1, wherein the first measurement line in which the first gap distance is measured by the first sensor being parallel to and not identical to the second measurement line in which the second gap distance is measured by the second sensor, and
wherein the distance calculator calculates a parallel object length between the first and second object positions in a direction parallel to the first and second measurement lines on the basis of the first and second gap distances, and calculates one of the candidate object lengths on the basis of the parallel object length and a perpendicular object length between the first and second object positions in a direction perpendicular to the first and second measurement lines.

12. The linear measurement apparatus according to claim 1, further comprising:
an angle calculator for calculating an angle of a line between the first and second noncontact distance measuring sensors with respect to the frame on the basis of a distance between the first and second sensors in a first direction and a distance between the first and second sensors in a second direction perpendicular to the first direction; and
sensor angle adjusters each for adjusting an angle of a measurement line of one of the first and second sensors on the basis of the angle so that the first measurement line in which the first gap distance is measured by the first sensor is identical to the second measurement line in which the second gap distance is measured by the second sensor.

13. The linear measurement apparatus according to claim 1, further comprising a frame-size adjustment mechanism for permitting a size of the frame to be adjusted.

14. The linear measurement apparatus according to claim 1, further comprising a frame-inclination adjustment mechanism for permitting an inclination of the frame to be adjusted with respect to the measured object.

15. The linear measurement apparatus according to claim 1, further comprising:
a display for displaying the maximum object length; and
a display controller for controlling the display such that the display holds the displayed maximum object length for a period of time.

16. The linear measurement apparatus according to claim 1, further comprising:
a display; and
a display controller for controlling the display such that a cross section of the measured object defined by the first object positions and the second object positions is displayed as a two-dimensional image on the basis of the first gap distances and the second gap distances measured at the measuring unit.

17. The linear measurement apparatus according to claim 1, further comprising:
an additional measuring unit comprising at least a third noncontact distance measuring sensor supported at the frame, the third sensor emitting light, receiving the light reflected from the measured object or a surface on which the measured object is placed, and generating a signal corresponding to a distance from the third sensor to the measured object or a surface on which the measured object is placed, so that the third sensor measures a third gap distance between the third sensor and a measured position in a third measurement line, the additional measuring unit measuring a plurality of third gap distances to a plurality of measured positions in a plurality of parallel third measurement lines lying on a plane identical to that in which the first and second measurement lines lie;
a measured-object-end detector for detecting a first end and a second end of the measured object on the basis of the plurality of third gap distances; and
a length calculator for calculating a length of the measured object between the first and second ends of the measured object,
wherein the maximum selector selects the maximum object length from among the length of the measured object and the plurality of candidate object lengths, instead of or in addition to selecting a maximum from among the plurality of candidate object lengths.

18. A linear measurement apparatus comprising:
a supporting member that can be disposed in proximity to a measured object;
a measuring unit comprising at least one noncontact distance measuring sensor supported at the supporting member, the sensor emitting light, receiving the light reflected from the measured object or a surface on which the measured object is placed, and generating a signal corresponding to a distance from the sensor to the measured object or a surface on which the measured object is placed, so that the sensor measures a gap distance between the sensor and a measured position in a measurement line, the measuring unit measuring a plurality of gap distances to a plurality of measured positions in a plurality of parallel measurement lines;
a reference light emitter located at the supporting member for irradiating reference light onto the measured object in order to facilitate deployment of the linear measurement apparatus with respect to a reference position of the measured object;
a measured-object-end detector for detecting a first end and a second end of the measured object on the basis of an amount of each of the plurality of gap distances, the first end and the second end being located on a line traversing the parallel measurement lines of the measuring unit; and
a length calculator for calculating a length of the measured object between the first and second ends of the measured object.

19. The linear measurement apparatus according to claim 18, further comprising a driving mechanism for moving the noncontact distance measuring sensor with respect to the supporting member, wherein the sensor measures a plurality of gap distances to a plurality of measured positions in a plurality of parallel measurement lines.

20. The linear measurement apparatus according to claim 19, further comprising a measurement terminator for terminating the sensor measuring the gap distance when the measured-object-end detector has detected that the sensor has reached the second end of the measured object after the sensor passed the first end of the measured object.

21. The linear measurement apparatus according to claim 19, wherein the measured-object-end detector determines that the sensor has reached the first end of the measured object when the sensor measures a gap distance that is less than a threshold or outputs an error signal, and wherein the measured-object-end detector determines that the sensor has reached the second end of the measured object when the sensor measures a gap distance that is greater than a threshold or outputs an error signal.

22. The linear measurement apparatus according to claim 18, further comprising:
- a manual interface by which an operator instructs to start and stop the sensor;
- a measurement starter for starting the sensor measuring the gap distance when the operator has instructed to start the sensor; and
- a measurement terminator for terminating the sensor measuring the gap distance when the operator has instructed to stop the sensor.

23. The linear measurement apparatus according to claim 18, further comprising a supporting-member-size adjustment mechanism for permitting a size of the supporting member to be adjusted.

24. The linear measurement apparatus according to claim 18, wherein the measuring unit comprising a plurality of the noncontact distance measuring sensors fixedly supported at the supporting member for measuring a plurality of gap distances to a plurality of measured positions in a plurality of parallel measurement lines, respectively.

25. The linear measurement apparatus according to claim 18, wherein the supporting member is of a shape in which one side is open, the supporting member having a pair of legs and a connection part connecting the legs, the noncontact distance measuring sensor being supported on the connection part.

26. The linear measurement apparatus according to claim 18, further comprising a supporting-member-inclination adjustment mechanism for permitting an inclination of the supporting member to be adjusted with respect to the measured object.

27. The linear measurement apparatus according to claim 18, further comprising:
- a display for displaying the length of the measured object; and
- a display controller for controlling the display such that the display holds the displayed length of the measured object for a period of time.

28. The linear measurement apparatus according to claim 18, further comprising:
- a display; and
- a display controller for controlling the display such that the measured positions are displayed as a two-dimensional image on the basis of the gap distances measured at the measuring unit.

* * * * *